US010450361B2

(12) United States Patent
Robblee et al.

(10) Patent No.: US 10,450,361 B2
(45) Date of Patent: Oct. 22, 2019

(54) METHODS RELATED TO CTLA4-FC FUSION PROTEINS

(71) Applicant: Momenta Pharmaceuticals, Inc., Cambridge, MA (US)

(72) Inventors: John Robblee, Cambridge, MA (US); Xiaomei He, Cambridge, MA (US); Yan Yin, Cambridge, MA (US); Yin Yin Lin, Cambridge, MA (US); Brian Collins, Cambridge, MA (US); Jennifer Murphy, Cambridge, MA (US); Ganesh Kaundinya, Cambridge, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 163 days.

(21) Appl. No.: 14/404,939

(22) PCT Filed: May 31, 2013

(86) PCT No.: PCT/US2013/043786
§ 371 (c)(1),
(2) Date: Dec. 1, 2014

(87) PCT Pub. No.: WO2014/149067
PCT Pub. Date: Sep. 25, 2014

(65) Prior Publication Data
US 2015/0368317 A1  Dec. 24, 2015

Related U.S. Application Data

(60) Provisional application No. 61/799,682, filed on Mar. 15, 2013.

(51) Int. Cl.
*C07K 14/705* (2006.01)
*C07K 16/28* (2006.01)

(52) U.S. Cl.
CPC .... *C07K 14/70521* (2013.01); *C07K 2319/30* (2013.01)

(58) Field of Classification Search
None
See application file for complete search history.

(56) References Cited

U.S. PATENT DOCUMENTS

| | | |
|---|---|---|
| 4,859,449 A | 8/1989 | Mattes |
| 5,047,335 A | 9/1991 | Paulson et al. |
| 5,068,190 A | 11/1991 | Horiuchi et al. |
| 5,234,905 A | 8/1993 | Kolhouse et al. |
| 5,340,453 A | 8/1994 | Jackson |
| 5,360,817 A | 11/1994 | von Izstein et al. |
| 5,370,872 A | 12/1994 | Cryz et al. |
| 5,411,942 A | 5/1995 | Widmer et al. |
| 5,456,909 A | 10/1995 | Marsh, Jr. et al. |
| 5,459,031 A | 10/1995 | Blumen et al. |
| 5,500,342 A | 3/1996 | Miyamura et al. |
| 5,510,261 A | 4/1996 | Goochee et al. |
| 5,554,730 A | 9/1996 | Woiszwillo et al. |
| 5,559,103 A | 9/1996 | Gaeta et al. |
| 5,567,684 A | 10/1996 | Ladisch et al. |
| 5,663,355 A | 9/1997 | Ganem et al. |
| 5,723,583 A | 3/1998 | Seed et al. |
| 5,753,454 A | 5/1998 | Lee |
| 5,759,823 A | 6/1998 | Wong et al. |
| 5,856,143 A | 1/1999 | Nilsson |
| 5,879,912 A | 3/1999 | Roth |
| 5,945,322 A | 8/1999 | Gotschlich |
| 6,030,815 A | 2/2000 | DeFrees et al. |
| 6,048,707 A | 4/2000 | Klock, Jr. |
| 6,096,555 A | 8/2000 | Hermentin et al. |
| 6,132,994 A | 10/2000 | Tawada et al. |
| 6,156,547 A | 12/2000 | Roth |
| 6,159,954 A | 12/2000 | Maruyama et al. |
| 6,190,522 B1 | 2/2001 | Haro |
| 6,218,149 B1 | 4/2001 | Morrison et al. |
| 6,261,805 B1 | 7/2001 | Wood |
| 6,274,568 B1 | 8/2001 | Schnaar et al. |
| 6,280,989 B1 | 8/2001 | Kapitonov et al. |
| 6,284,516 B1 | 9/2001 | Pollock et al. |
| 6,358,710 B1 | 3/2002 | Graves et al. |
| 6,597,996 B1 | 7/2003 | Venkataraman et al. |
| 7,364,736 B2 | 4/2008 | Boyle et al. |
| 8,034,906 B2 | 10/2011 | Borhani et al. |
| 8,278,072 B1 | 10/2012 | Matta et al. |
| 8,524,217 B2 | 9/2013 | Presta et al. |
| 2002/0054878 A1 | 5/2002 | Lowman et al. |
| 2003/0157108 A1 | 8/2003 | Presta |
| 2004/0137106 A1 | 7/2004 | Ciccone |
| 2004/0138106 A1 | 7/2004 | Schultz et al. |
| 2004/0210396 A1 | 10/2004 | Fischer et al. |
| 2005/0054832 A1 | 3/2005 | Lazar et al. |

(Continued)

FOREIGN PATENT DOCUMENTS

| | | |
|---|---|---|
| CA | 2828905 A1 | 9/2012 |
| EP | 2233502 A1 | 9/2010 |

(Continued)

OTHER PUBLICATIONS

FDA "Guidance for Industry" publication "Quality Considerations in Demonstrating Biosimilarity to a Reference Protein Product," Feb. 2012, pp. 1-22.*

(Continued)

*Primary Examiner* — Shulamith H Shafer
(74) *Attorney, Agent, or Firm* — Fish & Richardson P.C.

(57) ABSTRACT

The present disclosure provides, in part, methods for evaluating, identifying, and/or producing (e.g., manufacturing) a CTLA4-Fc fusion protein, e.g., abatacept. In some instances, methods herein allow highly resolved evaluation of abatacept useful for, inter alia, manufacturing abatacept, characterizing abatacept, identifying and/or confirming abatacept, monitoring the structure of abatacept, comparing abatacept preparations made over time or made under different conditions, and/or controlling the structure of abatacept.

20 Claims, 1 Drawing Sheet
Specification includes a Sequence Listing.

(56) References Cited

U.S. PATENT DOCUMENTS

| | | |
|---|---|---|
| 2006/0040353 A1 | 2/2006 | Davidson et al. |
| 2006/0127950 A1 | 6/2006 | Bosques et al. |
| 2006/0252672 A1 | 11/2006 | Betenbaugh et al. |
| 2008/0261301 A1 | 10/2008 | Kanda et al. |
| 2009/0041770 A1 | 2/2009 | Chamberlain et al. |
| 2009/0053238 A1 | 2/2009 | Allan |
| 2009/0069232 A1 | 3/2009 | Callewaert et al. |
| 2009/0104603 A1 | 4/2009 | Satomaa et al. |
| 2009/0203550 A1 | 8/2009 | Venkataraman et al. |
| 2009/0226968 A1 | 9/2009 | Betenbaugh et al. |
| 2009/0252749 A1 | 10/2009 | Leister et al. |
| 2009/0258014 A1 | 10/2009 | Laterra et al. |
| 2009/0311732 A1 | 12/2009 | Rossi et al. |
| 2009/0317834 A1 | 12/2009 | Laine et al. |
| 2010/0048456 A1 | 2/2010 | DeFrees et al. |
| 2010/0081150 A1 | 4/2010 | Liu et al. |
| 2010/0113294 A1 | 5/2010 | Venkataraman et al. |
| 2010/0129843 A1 | 5/2010 | Parsons et al. |
| 2010/0136599 A1 | 6/2010 | Gandhe et al. |
| 2010/0144553 A1 | 6/2010 | Bosques et al. |
| 2010/0166774 A1 | 7/2010 | Dali et al. |
| 2010/0173323 A1 | 7/2010 | Strome et al. |
| 2011/0076277 A1 | 3/2011 | Ravetch et al. |
| 2011/0263828 A1 | 10/2011 | Wong et al. |
| 2011/0280873 A1 | 11/2011 | Presta et al. |
| 2012/0058111 A1 | 3/2012 | Ehlers et al. |
| 2012/0100575 A1 | 4/2012 | Taylor et al. |
| 2012/0295273 A1 | 11/2012 | Washburn et al. |

FOREIGN PATENT DOCUMENTS

| | | |
|---|---|---|
| JP | 2002-542787 A | 12/2002 |
| JP | 2005-509403 A | 4/2005 |
| WO | WO-00/65070 A2 | 11/2000 |
| WO | WO-01/80884 A1 | 11/2001 |
| WO | WO-02/00879 A2 | 1/2002 |
| WO | WO-02/076578 A1 | 10/2002 |
| WO | WO-2005/116221 A1 | 12/2005 |
| WO | WO-2007/011041 A1 | 1/2007 |
| WO | WO-2007/055916 A2 | 5/2007 |
| WO | WO-2007/076032 A2 | 7/2007 |
| WO | WO-2007/087384 A2 | 8/2007 |
| WO | WO-2007/117505 A2 | 10/2007 |
| WO | WO-2008/057634 A2 | 5/2008 |
| WO | WO-2008/063982 A2 | 5/2008 |
| WO | WO-2008/128228 A1 | 10/2008 |
| WO | WO-2008/130926 A2 | 10/2008 |
| WO | WO-2009/021708 A2 | 2/2009 |
| WO | WO-2009/058564 A2 | 5/2009 |
| WO | WO-2009/079382 A1 | 6/2009 |
| WO | WO-2010/130756 A1 | 11/2010 |
| WO | WO-2010/136492 A2 | 12/2010 |
| WO | WO-2010/138502 A2 | 12/2010 |
| WO | WO-2010/141855 A1 | 12/2010 |
| WO | WO-2011/103584 A2 | 8/2011 |
| WO | WO-2011/127322 A1 | 10/2011 |
| WO | WO-2011/127325 A1 | 10/2011 |
| WO | WO-2012/113863 A1 | 8/2012 |
| WO | WO-2012/120125 A1 | 9/2012 |
| WO | WO-2014/018747 A2 | 1/2014 |
| WO | WO-2014/052360 A2 | 4/2014 |
| WO | WO-2014/179601 A2 | 11/2014 |
| WO | WO-2015/057622 A1 | 4/2015 |

OTHER PUBLICATIONS

International Preliminary Report on Patentability for International Application No. PCT/US2013/043786, dated Sep. 15, 2015 (12 pages).

Ahn et al., "Separation of 2-aminobenzamide labeled glycans using hydrophilic interaction chromatography columns packed with 1.7 μm sorbent," J Chromatogr. 878:403-8 (2010).

Chelius et al., "Formation of pyroglutamic acid from N-terminal glutamic acid in immunoglobulin gamma antibodies," Anal Chem. 78:2370-6 (2006).

Chen et al., "Gas-phase oligosaccharide nonreducing end (GONE) sequencing and structural analysis by reversed phase HPLC/mass spectrometry with polarity switching," J Am Soc Mass Spectrom. 20:1821-33 (2009).

Chen et al., "Analysis of N-glycans from recombinant immunoglobulin G by on-line reversed-phase high-performance liquid chromatography/mass spectrometry," Anal Biochem. 370:147-61 (2007).

Chumsae et al., "Identification and localization of unpaired cysteine residues in monoclonal antibodies by fluorescence labeling and mass spectrometry," Anal Chem. 81:6449-57 (2009).

Dick et al., "C-Terminal lysine variants in fully human monoclonal antibodies: investigation of test methods and possible causes," Biotechnol Bioeng. 100(6):1132-43 (2008).

Forrer et al., "Chip-based gel electrophoresis method for the quanitification of half-antibody species in IgG4 and their by- and degradation products," Anal Biochem. 334:81-8 (2004).

Goetze et al., "High-mannose glycans on the Fc region of therapeutic IgG antibodies increase serum clearance in humans," Glycobiology. 21(7):949-59 (2011).

Hokke et al., "Sialylated carbohydrate chains of recombinant human glycoproteins expressed in Chinese hamster ovary cells contain traces of N-glycolylneuraminic acid," FEBS Lett. 275(1-2):914 (1990).

Miller et al., "Characterization of site-specific glycation during process development of a human therapeutic monoclonal antibody," J Pharm Sci. 100(7):2543-50 (2011).

Shang et al., "Development and application of a robust N-glycan profiling method for heightened characterization of monoclonal antibodies and related glycoproteins," J Pharm Sci. 103(7):196778 (2014).

Wang et al., "Characterization and comparison of disulfide linkages and scrambling patterns in therapeutic monoclonal antibodies: using LC-MS with electron transfer dissociation," Anal Chem. 83:3133-40 (2011).

Xie et al., "Rapid comparison of a candidate biosimilar to an innovator monoclonal antibody with advanced liquid chromatography and mass spectrometry technologies," MAbs. 2(4):379-94 (2010).

Yan et al., "Analysis of post-translational modifications in recombinant monoclonal antibody IgG1 by reversed-phase liquid chromatography/mass spectrometry," J Chromatogr. 1164(1-2):153-61 (2007).

Third-Party Observation pursuant to Rule 114(2) EPC for European Patent Application No. 13796989.5, dated Jun. 22, 2016 (14 pages).

Lattová et al., "Alterations in glycopeptides associated with herceptin treatment of human breast carcinoma MCF-7 and T-lymphoblastoid cells," Mol Cell Proteomics. 10(9):M111.007765 (2011).

Schellekens, H., "Biosimilar therapeutics—what do we need to consider?" NDT Plus. 2(Suppl_1):i27-i36 (2009).

Schiestl et al., "Acceptable changes in quality attributes of glycosylated biopharmaceuticals." Nat Biotechnol. 29(4):310-2 (2011).

Tan et al., "Characterization and comparison of commercially available TNF receptor 2-Fc fusion protein products." Mabs. 4(6):761-74 (2012).

Zhang et al., "Glycoengineered Pichia produced anti-HER2 is comparable to trastuzumab in preclinical study." MAbs. 3(3):289-98 (2011).

"Glycosylation main approval issue with biosimilars," <http://gabionline.net/Conferences/Glycosylation-main-approval-issue-with-biosimilars>, dated Jan. 9, 2009, retrieved Jul. 18, 2016 (2 pages).

Misra, "Are biosimilars really generics?" Expert Opin Biol Ther. 10(4):489-94 (2010).

Roger, "Biosimilars: current status and future directions," Expert Opin Biol Ther. 10(7):1011-8 (2010).

Greer, "Biosimilar developers face a reference-product dilemma," <http://license.icopyright.net/user/viewFreeUse.act?fuid=MTYwMTg0NDk%3D>, retrieved on Apr. 9, 2012 (3 pages).

Hincal, "An introduction to safety issues in biosimilars/follow-on biopharmaceuticals," J Med CBR Def. 7 (18 pages) (2009).

(56) References Cited

OTHER PUBLICATIONS

Kalodiki et al., "New and generic anticoagulants and biosimilars: safety considerations," Clin Appl Thromb Hemost. 17(2):136-9 (2011) (5 pages).
Nowicki, "Basic facts about biosimilars," Kidney Blood Press Res. 30:267-72 (2007).
Rader, "Nomenclature of new biosimilars will be highly controversial," BioProcess International. 9:28-32 (2011).
Schellekens at al., "Clinical comparability and European biosimilar regulations," Nat Biotechnol. 28(1):28-31 (2010).
Sekhon et al., "Biosimilars: an overview," Biosimilars. 2011(1):1-11 (2011).
Ahn et al., "Separation of 2-aminobenzamide labeled glycans using hydrophilic interaction chromatography columns packed with 1.7 µm sorbent," J Chromatogr B. 878:403-8 (2010).
Dick et al., "C-terminal lysine variants in fully human monoclonal antibodies: investigation of test methods and possible causes," Biotechnol Bioeng. 100:1132-43 (2008).
Stadlmann et al., "Analysis of immunoglobulin glycosylation by LC-ESI-MS of glycopeptides and oligosaccharides," Proteomics. 8:2858-71 (2008).
Joziasse et al., "Branch specificity of bovine colostrum CMP-sialic acid: Gal beta 1—4GlcNAc-R alpha 2—6-sialyltransferase. Sialylation of bi-, tri-, and tetraantennary oligosaccharides and glycopeptides of the N-acetyllactosamine type," J Biol Chem. 262(5):2025-33 (1987).
Raymond et al., Production of Highly Sialylated Monoclonal Antibodies. *Biochemistry, Genetics and Molecular Biology-Glycosylation*. Stefana Petrescu, 397-418 (2012).
Barb et al., "Branch specific sialylation of IgG-Fc Glycans by ST6Gal-I." Biochemistry. 48(41):9705-7 (2009) (6 pages).
Raju, "Terminal sugars of Fc glycans influence antibody effector functions of IgGs," Curr Opin Immunol. 20(4):471-8 (2008).
Kaneko et al., "Anti-inflammatory activity of immunoglobulin G resulting from Fc sialylation." Science. 313(5787):670-3 (2006).
Anthony et. al., "A novel role for the IgG Fc glycan: the anti-inflammatory activity of sialylated IgG Fcs," J Clin Immunol. 30(Suppl 1):S9-14 (2010).
Parmley, Sweetening Immunoglobulins. *Biocentury Innovations*. Bernstein (2015)(2 pages).
Cummings et al., Antibodies and Lectins in Glycan Analysis. *Essentials of Glycobiology*. Varki A, Cummings RD, Esko JD et al., 1-17 (2009).
Barb et al., "NMR characterization of immunoglobulin G Fc glycan motion on enzymatic sialylation." Biochemistry. 51(22):4618-26 (2012).
Gilar et al., "Characterization of glycoprotein digests with hydrophilic interaction chromatography and mass spectrometry." Anal Biochem. 417(1):80-8 (2011).
Barb et al., Supporting Information for "Branch specific sialylation of IgG-Fc Glycans by ST6Gal-I," Biochemistry. 48(41):9705-7 (2009) (8 pages).
Rüdiger et al., "Breaking the sugar code: six levels of affinity regulation in glycan-lectin interaction," Cracking the Sugar Code by Navigating the Glycospace. Germany, 11-28 (2011).
Lance et al., "Isolation and characterization of a partial cDNA for a human sialyltransferase." Biochem Biophys Res Commun. 164(1):225-32 (1989).
Extended European Search Report for European Application No. 13878846.8, dated Oct. 22, 2015 (6 pages).
Extended European Search Report for European Application No. 14792116.7, dated Oct. 21, 2016 (9 pages).
Akiyama et al., "Analysis of the role of glycosylation of the human fibronectin receptor", J. Biol. Chem. vol. 264(30):18011-8 (1989).
Andrade et al., "Solid-phase oligosaccharide synthesis: preparation of complex structures using a novel linker and different glycosylating agents", Org Lett. 1(11):1811-4 (1999).
Anumula, "Advances in fluorescence derivatization methods for high-performance liquid chromatographic analysis of glycoprotein carbohydrates", Anal Biochem. 350(1):1-23 (2006).
Baker et al., "Metabolic control of recombinant protein N-glycan processing in NS0 and CHO cells", Biotechnol Bioeng. 73(3):188-202 (2001).
Becker et al., "Fucose: biosynthesis and biological function in mammals," Glycobiology. 13(7):41R-53R (2003).
Bohne et al., "Sweet—WWW-based rapid 3D construction of oligo- and polysaccharides", Bioinformatics. 15(9): 767-768 (1999).
Bollati-Fogolin et al., "Temperature reduction in cultures of hGM-CSF-expressing CHO cells: effect on productivity and product quality", Biotechnol Prog. 21(1):17-21 (2005).
Bowman et al., "Biosynthesis of L-selectin ligands: sulfation of sialyl Lewis x-related oligosaccharides by a family of GlcNAc-6-sulfotransferases", Biochemistry. 40(18):5382-91 (2001).
Breidenbach et al., "Targeted metabolic labeling of yeast N-glycans with unnatural sugars," Proc Natl Acad Sci USA. 107(9):3988-93 (2010).
Broschat et al., "Purification and characterization of GDP-D-mannose 4,6-dehydratase from porcine thyroid", Eur J Biochem. 153(2):397-401 (1985).
Joosten et al., "Effect of culture conditions on the degree of sialylation of a recombinant glycoprotein expressed in insect cells", Biotechnol Prog. 19(3):739-49 (2003).
Cabrera et al., "Influence of culture conditions on the N-glycosylation of a monoclonal antibody specific for recombinant hepatitis B surface antigen", Biotechnol Appl Biochem. 41(Pt 1):67-76 (2005).
Chen et al., "Independent Lec1A CHO glycosylation mutants arise from point mutations in N-acetylglucosaminyltransferase I that reduce affinity for both substrates. Molecular consequences based on the crystal structure of GlcNAc-TI", Biochemistry. 40(30):8765-72 (2001).
Chen et al., "T cell receptor signaling co-regulates multiple Golgi genes to enhance N-glycan branching," J Biol Chem. 284(47):32454-61 (2009).
Chen et al., "Effects of elevated ammonium on glycosylation gene expression in CHO cells", Metab Eng. 8(2):123-32 (2006).
Clark et al., "Gene-expression profiles for five key glycosylation genes for galactose-fed CHO cells expressing recombinant IL-4/13 cytokine trap", Biotechnol Bioeng. 90(5):568-77 (2005).
Cooper et al., "GlycoSuiteDB: a curated relational database of glycoprotein glycan structures and their biological sources. 2003 update", Nucleic Acids Res. 31(1):511-3 (2003).
Cooper et al., "GlycoSuiteDB: a new curated relational database of glycoprotein glycan structures and their biological sources", Nucleic Acids Res. 29(1):332-5 (2001).
Cox et al., "Glycan optimization of a human monoclonal antibody in the aquatic plant Lemna minor", Nat Biotechnol. 24(12):1591-7 (2006).
Crowell et al., "Amino acid and manganese supplementation modulates the glycosylation state of erythropoietin in a CHO culture system", Biotechnol Bioeng. 96(3):538-549 (2007) (29 pages).
Debray et al., Glycoprotein Analysis: General Methods. *Encyclopedia of Analytical Chemistry*. John Wiley & Sons, 1-39 (2006).
Donaldson et al., "The use of lectins to select subpopulations of insect cells", Biotechnol Bioeng. 64(5):616-9 (1999).
Dorka, Penny, Thesis: "Modelling Batch and Fed-Batch Mammalian Cell Cultures for Optimizing MAb Productivity," Master of Science, University of Waterloo, 2007.
Drecktrah et al., "Inhibition of a Golgi complex lysophospholipid acyltransferase induces membrane tubule formation and retrograde trafficking," Mol Biol Cell. 14(8):3459-69 (2003).
Communication pursuant to Article 96(2) for European Patent Application No. 02773390.6, dated Oct. 30, 2007 (3 pages).
Extended European Search Report for European Patent Application No. 12158671.3, dated Mar. 1, 2013 (19 pages).
Extended European Search Report for European Patent Application No. 11766759.2, dated Aug. 19, 2013 (15 pages).
Extended European Search Report for European Patent Application No. 11766762.6, dated Jan. 28, 2014 (12 pages).
Fareed, J., "S-9-10 synthetic and biotechnology derived glycomimetics. Impact on drug development", Abstract of Presentation for Proteoglycan Forum; Hamamatsu, Japan (1 page) (2000).

(56) References Cited

OTHER PUBLICATIONS

"Scientific Considerations in Demonstrating Biosimilarity to a Reference Product: Guidance for Industry," Food and Drug Administration (25 pages) (2012).
Ferrara et al., "Modulation of therapeutic antibody effector functions by glycosylation engineering: influence of golgi enzyme localization domain and co-expression of heterologous beta1, 4-N-acetylglucosaminyltransferase III and golgi alpha-mannosidase II," Biotechnol Bioeng. 93(5):851-861 (2006).
Fitz et al., "Combined use of subtilisin and N-acetyl neuraminic acid aldolase for the synthesis of a fluorescent sialic acid," J Org Chem. 59(26):8279-80 (1994).
Fleischer, B., "Mechanism of glycosylation in the Golgi apparatus," J Histochem Cytochem. 31(8):1033-40 (1983).
Forno et al., "N- and O-linked carbohydrates and glycosylation site occupancy in recombinant human granulocyte-macrophage colony-stimulating factor secreted by a Chinese hamster ovary cell line," Eur J Biochem. 271(5):907-19 (2004).
Fukuda et al., "Survival of recombinant erythropoietin in the circulation: the role of carbohydrates", Blood. 73(1):84-89 (1989).
Gates et al., "Glycobiology Analysis Manual," <http://www.sigmaaldrich.com/life-science/proteomics/post-translational-analysis/glycosylation/glycoprotein-analysis-manual.html>, retrieved on Nov. 23, 2016 (132 pages).
Gawlitzek et al., "Ammonium alters N-glycan structures of recombinant TNFR-IgG: degradative versus biosynthetic mechanisms", Biotechnol Bioeng. 68(6):637-46 (2000).
Gawlitzek et al., "Characterization of changes in the glycosylation pattern of recombinant proteins from BHK-21 cells due to different culture conditions", J Biotechnol. 42(2):117-131 (1995).
Goldman et al., "Monitoring recombinant human interferon-gamma N-glycosylation during perfused fluidized-bed and stirred-tank batch culture of CHO cells", Biotechnol Bioeng. 60(5):596607 (1998).
Gu et al., "Improvement of interferon-gamma sialylation in Chinese hamster ovary cell culture by feeding of N-acetylmannosamine", Biotechnol Bioeng. 58(6):642-48 (1998).
Hara et al., "Determination of mono-O-acetylated N-acetylneuraminic acids in human and rat sera by fluorometric high-performance liquid chromatography," Anal Biochem. 179(1):162-6 (1989).
Imai-Nishiya et al., "Double knockdown of alpha1,6-fucosyltransferase (FUT8) and GDP-mannose 4,6-dehydratase (GMD) in antibody-producing cells: a new strategy for generating fully non-fucosylated therapeutic antibodies with enhanced ADCC", BMC Biotechnol. 7:84 (2007) (13 Pages).
Hendrick et al., "Increased productivity of recombinant tissular plasminogen activator (t-PA) by butyrate and shift of temperature: a cell cycle phases analysis", Cytotechnology. 36(1-3):71-83 (2001).
Hewitt et al., "Solution and solid-support synthesis of a potential leishmaniasis carbohydrate vaccine", J Org Chem. 66(12):4233-43 (2001).
Hills et al.. "Metabolic control of recombinant monoclonal antibody N-glycosylation in GS-NS0 cells," Biotechnol Bioeng. 75(2):239-51 (2001).
Hirabayashi et al., "Separation technologies for glycomics", J Chromatog B Analyst Technol Biomed Life Sci. 771(1-2):67-87 (2002) (Abstract Only) (2 pages).
Hoja-Lukowicz et al., "High-mannose-type oligosaccharides from human placental arylsulfatase A are core fucosylated as confirmed by MALDI MS", Glycobiology. 10(6):551-7 (2000).
Hosoi et al., "Modulation of oligosaccharide structure of a pro-urokinase derivative (pro-UK delta GS1) by changing culture conditions of a lymphoblastoid cell line Namalwa KJM-1 adapted to serum-free medium," Cytotechnology. 19(2):125-35 (1996).
Hossler et al., "Systems analysis of N-glycan processing in mammalian cells," PLoS One. 2(8):e713 (2007) (17 pages).
Reitman et al., "Mouse lymphoma cell lines resistant to pea lectin are defective in fucose metabolism", J Biol Chem. 255(20):9900-6 (1980).
Restelli et al., "The effect of dissolved oxygen on the production and the glycosylation profile of recombinant human erythropoietin produced from CHO cells", Biotechnol Bioeng. 94(3):481-94 (2006).
Ripka et al., "Two Chinese hamster ovary glycosylation mutants affected in the conversion of GDP-mannose to GDP-fucose," Arch Biochem Biophys. 249(2):533-45 (1986).
Ritzenthaler et al., "Reevaluation of the effects of brefeldin A on plant cells using tobacco Bright Yellow 2 cells expressing Golgi-targeted green fluorescent protein and COPI antisera," Plant Cell. 14(1):237-61 (2002).
Robinson et al., "Characterization of a recombinant antibody produced in the course of a high yield fed-batch process," Biotechnol Bioeng. 44(6):727-35 (1994).
Rodriguez et al., "Enhanced production of monomeric interferon-beta by CHO cells through the control of culture conditions," Biotechnol Prog. 21(1):22-30 (2005).
Santell et al., "Aberrant metabolic sialylation of recombinant proteins expressed in Chinese hamster ovary cells in high productivity cultures," Biochem Biophys Res Commun. 258(1):132-7 (1999).
Sasaki et al.,"Site-specific glycosylation of human recombinant erythropoietin: analysis of glycopeptides or peptides at each glycosylation site by fast atom bombardment mass spectrometry," Biochemistry. 27(23):8618-26 (1988).
Schulz et al., "Mediators of galactose sensitivity in UDP-galactose 4'-epimerase-impaired mammalian cells," J Biol Chem. 280(14):13493-502 (2005).
Schuster et al., "Improved effector functions of a therapeutic monoclonal Lewis Y-specific antibody by glycoform engineering," Cancer Res. 65(17):7934-41 (2005).
Search Report for Chinese Patent Application No. 201180022319.9, dated Sep. 30, 2012 (4 pages).
Senger et al., "Effect of shear stress on intrinsic CHO culture state and glycosylation of recombinant tissue-type plasminogen activator protein," Biotechnol Prog. 19(4):1199-209 (2003).
Serrato et al., "Heterogeneous conditions in dissolved oxygen affect N-glycosylation but not productivity of a monoclonal anitbody in hybridoma cultures", Biotechnol Bioeng. 88(2):176-188 (2004).
Shames et al., "CMP-N-acetylneuraminic acid synthetase of *Escherichia coli*: high level expression, purification and use in the enzymatic synthesis of CMP-N-acetylneuraminic acid and CMP-neuraminic acid derivatives", Glycobiology. 1(2):187-191 (1991).
Sherman, Rachel E., "Biosimilar Biological Products". Biosimilar Guidance Webinar. Food and Drug Administration (22 pages) (2012).
Shinkawa et al., "The absence of fucose but not the presence of galactose or bisecting N-acetylglucosamine of human IgG1 complex-type oligosaccharides shows the critical role of enhancing antibody-dependent cellular cytotoxicity," J Biol Chem. 278(5):3466-73 (2003).
Sokolowski et al., "Conformational analysis of biantennary glycans and molecular modeling of their complexes with lentil lectin", J Mol Graph Model. 15(1):37-42 (1997).
Sparks et al., "Synthesis of potential inhibitors of hemagglutination by Influenza virus: chemoenzymic preparation of N-5 analogs of N-acetylneuraminic acid", Tetrahedron. 49(1):1-12 (1993).
Spearman et al., "Production and glycosylation of recombinant beta-interferon in suspension and cytopore microcarrier cultures of CHO cells", Biotechnol Prog. 21(1):31-9 (2005).
Srinivas et al., "Pharmacokinetics and pharmacodynamics of CTLA4Ig (BMS-188667), a novel immunosuppressive agent, in monkeys following multiple doses," J Pharm Sci. 85(1):1-4 (1996).
Srinivas et al., "Assessment of dose proportionality, absolute bioavailability, and immunogenicity response of CTLA4Ig (BMS-188667), a novel immunosuppressive agent, following subcutaneous and intravenous administration to rats," Pharm Res. 14(7):911-6 (1997).
Sung et al., "Effect of sodium butyrate on the production, heterogeneity and biological activity of human thrombopoietin by recombinant Chinese hamster ovary cells," J Biotechnol. 112(3):323-35 (2004).
Supplementary Partial European Search Report for European Patent Application No. 02773390.6, dated Aug. 31, 2004 (4 pages).
Takeuchi et al.,"Structures and functional roles of the sugar chains of human erythropoietins," Glycobiology. 1(4):337-346 (1991).

(56) References Cited

OTHER PUBLICATIONS

Tran et al., "Separation of carbohydrate-mediated microheterogeneity of recombinant human erythropoietin by free solution capillary electrophoresis. Effects of pH, buffer type and organic additives," J Chromatogr. 542(2):459-71 (1991).
Trombetta et al., "Glycoprotein reglucosylation and nucleotide sugar utilization in the secretory pathway: identification of a nucleoside diphosphatase in the endoplasmic reticulum," EMBO J. 18(12):3282-92 (1999).
Trummer et al., "Process parameter shifting: Part I. Effect of DOT, pH, and temperature on the performance of Epo-Fc expressing CHO cells cultivated in controlled batch bioreactors," Biotechnol Bioeng. 94(6)1 033-44 (2006).
Umana et al., "Engineered glycoforms of an antineuroblastoma IgG1 with optimized antibody-dependent cellular cytotoxic activity," Nat Biotechnol. 17(2):176-80 (1999).
Van Berkel et al., "N-linked glycosylation is an important parameter for optimal selection of cell lines producing biopharmaceutical human IgG," Biotechnol Prog. 25(1):244-51 (2009).
Van Den Nieuwenhof et al., "Recombinant glycodelin carrying the same type of glycan structures as contraceptive glycodelin-A can be produced in human kidney 293 cells but not in Chinese hamster ovary cells," Eur J Biochem. 267(15):4753-62 (2000).
Varki, A., "Radioactive tracer techniques in the sequencing of glycoprotein oligosaccharides," FASEB J. 5(2): 226-35 (1991).
Venkataraman et al., "Sequencing complex polysaccharides," Science. 286(5439):537-42 (1999).
Von Der Lieth, "Expanding proteomics to glycobiology: biocomputing approaches understanding the function of sugar," Pacific Symposium on Biocomputing; Kauai, Hawaii (Abstract only) (2 pages) (2002).
Wang et al., "EDEM an ER quality control receptor," Nat Struct Biol. 10(5):319-21 (2003).
Watson et al., "Capillary electrophoretic separation of human recombinant erythropoietin (r-HuEPO) glycoforms," Anal Biochem. 210(2):389-93 (1993).
Watson et al., "Structure determination of the intact major sialylated oligosaccharide chains of recombinant human erythropoietin expressed in Chinese hamster ovary cells," Glycobiology. 4(2):227-37 (1994).
Webb et al., "Structural characterization of intact, branched oligosaccharides by high performance liquid chromatography and liquid secondary ion mass spectrometry," Anal Biochem. 169(2):337-49 (1988).
Weiner et al., "A sensitive enzyme immunoassay for the quantitation of human CTLA4Ig fusion protein in mouse serum: pharmacokinetic application to optimizing cell line selection," J Pharm Biomed Anal. 15(5):571-9 (1997).
Wong et al., "Impact of dynamic online fed-batch strategies on metabolism, productivity and N-glycosylation quality in CHO cell cultures," Biotechnol Bioeng. 89(2):164-77 (2005).
Wopereis et al., "Mechanisms in protein O-glycan biosynthesis and clinical and molecular aspects of protein O-glycan biosynthesis defects: a review," Clin Chem. 52(4):574-600 (2006).
Wright et al., "In vivo trafficking and catabolism of IgG1 antibodies with Fc associated carbohydrates of differing structure," Glycobiology. 10(12)1 347-55 (2000).
Yang et al., "Bio-basis function neural network for prediction of protease cleavage sites in proteins," IEEE Trans Neural Netw. 16(1):263-74 (2005).
Yang et al., "Achievement of high cell density and high antibody productivity by a controlled-fed perfusion bioreactor process," Biotechnol Bioeng. 69(1):74-82 (2000).
Yang et al., "Effect of ammonia on the glycosylation of human recombinant erythropoietin in culture," Biotechnol Prog. 16(5):751-9 (2000).
Ye et al., "N-glycan branching requirement in neuronal and postnatal viability," Glycobiology. 14(6):547-58 (2004).
Yoon et al., "Effect of culture pH on erythropoietin production by Chinese hamster ovary cells grown in suspension at 32.5 and 37.0 degrees C," Biotechnol Bioeng. 89(3):345-56 (2005).
Yoon et al., "Effect of simultaneous application of stressful culture conditions on specific productivity and heterogeneity of erythropoietin in Chinese hamster ovary cells," Biotechnol Prog. 20(4):1293-6 (2004).
Yuen et al., "Relationships between the N-glycan structures and biological activities of recombinant human erythropoietins produced using different culture conditions and purification procedures," Br J Haematol. 121(3):511-26 (2003).
Yuk et al., "Changes in the overall extent of protein glycosylation by Chinese hamster ovary cells over the course of batch culture", Biotechnol Appl Biochem. 36(Pt 2):133-40 (2002).
Yuk et al., "Glycosylation by Chinese hamster ovary cells in dolichol phosphate-supplemented cultures," Biotechnol Appl Biochem. 36(Pt 2):141-7 (2002).
Zhang et al., "Quantitative analysis and process monitoring of site-specific glycosylation microheterogeneity in recombinant human interferon-gamma from Chinese hamster ovary cell culture by hydrophilic interaction chromatography," J Chromatogr B Biomed Sci Appl. 712(1-2):7382 (1998).
International Preliminary Report on Patentability for International Patent Application No. PCT/US2010/036058, dated Nov. 29, 2011 (12 pages).
International Preliminary Report on Patentability for International Patent Application No. PCT/US2011/031637, dated Oct. 9, 2012 (12 pages).
International Preliminary Report on Patentability for International Patent Application No. PCT/US2012/028759, dated Jan. 14, 2014 (7 pages).
International Preliminary Report on Patentability for International Patent Application No. PCT/US2008/060354, dated Apr. 2, 2009 (6 pages).
International Preliminary Report on Patentability for International Patent Application No. PCT/US2011/031641, dated Oct. 9, 2012 (7 pages).
International Search Report and Written Opinion for International Patent Application No. PCT/US2010/031637, dated Jun. 16, 2010 (10 pages).
International Search Report and Written Opinion for International Patent Application No. PCT/US2013/043670, dated Jan. 7, 2014 (18 pages).
International Search Report and Written Opinion for International Patent Application No. PCT/US13/43696, dated Jan. 17, 2014 (21 pages).
International Search Report and Written Opinion for International Patent Application No. PCT/US2013/43671, dated Jan. 7, 2014 (20 pages).
International Search Report for International Patent Application No. PCT/US02/29285, dated Dec. 23, 2002 (3 pages).
International Search Report for International Patent Application No. PCT/US04/04423, dated Dec. 28, 2004 (2 pages).
International Search Report for International Patent Application No. PCT/US10/36058, dated Nov. 19, 2010 (4 pages).
International Search Report and Written Opinion for International Patent Application No. PCT/US2011/031641, dated Aug. 17, 2011 (16 pages).
International Search Report and Written Opinion for International Patent Application No. PCT/US2013/043667, dated Jan. 13, 2014 (21 pages).
International Search Report and Written Opinion for International Patent Application No. PCT/US13/43676, dated Jan. 16, 2014 (22 pages).
International Search Report and Written Opinion for International Patent Application No. PCT/US13/43693, dated Jan. 13, 2014 (15 pages).
International Search Report and Written Opinion for International Patent Application No. PCT/US12/28759, dated Sep. 4, 2012 (10 pages).
International Search Report and Written Opinion for International Patent Application No. PCT/US13/43674, dated Jan. 15, 2014 (20 pages).
International Search Report and Written Opinion for International Patent Application No. PCT/US13/43675, dated Dec. 23, 2013 (22 pages).

(56) References Cited

OTHER PUBLICATIONS

Jabs et al., "Fast and Extensive Mass Spectrometry Characterization of Theraputic mAbs: The Panitumumab Case Study," CASSS Mass Spec Meeting, Poster 125 (1 page) (2012).

Nam et al., "The effects of culture conditions on the glycosylation of secreted human placental alkaline phosphatase produced in Chinese hamster ovary cells," Biotechnol Bioeng. 100(6):117892 (2008).

Kakehi et al., "Analysis of glycoproteins, glycopeptides and glycoprotein-derived oligosaccharides by high-performance capillary electrophoresis," J Chromatogr. 720(1-2):377-93 (1996).

Kanda et al., "Comparison of biological activity among nonfucosylated therapeutic IgG1 antibodies with three different N-linked Fc oligosaccharides: the high-mannose, hybrid, and complex types," Glycobiology. 17(1):104-18 (2006).

Kanda et al., "Establishment of a GDP-mannose 4,6-dehydratase (GMD) knockout host cell line: A new strategy for generating completely non-fucosylated recombinant therapeutics," Journal of Biotechnol. 130(3):300-10 (2007) (Abstract Only).

Kawashima et al., "Tyrosine kinase activity of epidermal growth factor receptor is regulated by GM3 binding through carbohydrate to carbohydrate interactions," J Biol Chem. 284(10):6147-55 (2009).

Keiser et al., "Direct isolation and sequencing of specific protein-binding glycosaminoglycans," Nat Med. 7(1):123-8 (2001).

Keppler et al., "Biosynthetic modulation of sialic acid-dependent virus-receptor interactions of two primate polyoma viruses," J Biol Chem. 270(3):1308-14 (1995).

Kim et al., "Production and N-glycan analysis of secreted human erythropoietin glycoprotein in stably transfected *Drosophila* S2 cells," Biotechnol Bioeng. 92(4):452-61 (2005).

Kosa et al., "Modification of cell surfaces by enzymatic introduction of special sialic acid analogues," Biochem Biophys Res Commun. 190(3):914-20 (1993).

Krapp et al., "Structural analysis of human IgG-Fc glycoforms reveals a correlation between glycosylation and structural integrity," J Mol Biol. 325(5):979-89 (2003).

Kunkel et al., "Comparisons of the glycosylation of a monoclonal antibody produced under nominally identical cell culture conditions in two different bioreactors," Biotechnol Prog. 16(3):46270 (2000).

Kunkel et al., "Dissolved oxygen concentration in serum-free continuous culture affects N-linked glycosylation of a monoclonal antibody," J Biotechnol. 62(1):55-71 (1998).

Le Floch et al., "HPCE monitoring of the N-glycosylation pattern and sialylation of murine erythropoietin produced by CHO cells in batch processes," Biotechnol Prog. 20(3):864-71 (2004).

Lifely et al., "Glycosylation and biological activity of CAMPATH-1H expressed in different cell lines and grown under different culture conditions," Glycobiology. 5(8):813-22 (1995).

Lin et al., "Unusual stereoselectivity in sialic acid aldolase-catalyzed aldol condensations: synthesis of both enantiomers of high-carbon monosaccharides," J Am Chem Soc. 114(26):10138-45 (1992).

Lipscomb et al., "Effect of production method and gene amplification on the glycosylation pattern of a secreted reporter protein in CHO cells," Biotechnol Prog. 21(1):40-9 (2005).

Live et al., "Conformational influences of glycosylation of a peptide: a possible model for the effect of glycosylation on the rate of protein folding," Proc Natl Acad Sci USA. 93(23):12759-61 (1996).

Lopez-Avalos et al., "The UDPase activity of the Kluyveromyces lactis Golgi GDPase has a role in uridine nucleotide sugar transport into Golgi vesicles," Glycobiology. 11(5):413-22 (2001).

Macmillan et al.,"Selective in vitro glycosylation of recombinant proteins: semi-synthesis of novel homogeneous glycoforms of human erythropoietin," Chem Biol. 8(2):133-45 (2001).

Moran et al., "A systematic approach to the validation of process control parameters for monoclonal antibody production in fed-batch culture of a murine myeloma," Biotechnol Bioeng. 69(3):242-55 (2000).

Mueller et al., "Recombinant glycoprotein product quality in proliferation-controlled BHK-21 cells," Biotechnol Bioeng. 65(5):529-36 (1999).

Nairn et al., "Regulation of glycan structures in animal tissues: transcript profiling of glycan-related genes," J Biol Chem. 283(25):17298-313 (2008).

Nyberg et al., "Metabolic effects on recombinant interferon-gamma glycosylation in continuous culture of Chinese hamster ovary cells," Biotechnol Bioeng. 62(3):336-47 (1999).

Oh et al., "Effect of N-acetylcystein on butyrate-treated Chinese hamster ovary cells to improve the production of recombinant human interferon-beta-1a," Biotechnol Prog. 21(4):1154-64 (2005).

Pace et al., "Characterization of minor N-linked glycans on antibodies using endo H release and MALDI-mass spectrometry," Anal Lett. 42:1711-24 (2009).

Park et al., "Expression of carbamoyl phosphate synthetase I and ornithine transcarbamoylase genes in Chinese hamster ovary dhfr-cells decreases accumulation of ammonium ion in culture media," J Biotechnol. 81(2-3):129-40 (2000).

Plante et al., "Automated solid-phase synthesis of oligosaccharides," Science. 291(5508):1523- 7 (2001).

Plante et al., "Formation of beta-glucosamine and beta-mannose linkages using glycosyl phosphates," Org Lett. 2(24):3841-3 (2000).

Feasby et al., "Guidelines on the use of intravenous immune globulin for neurologic conditions," Transfus Med Rev. 21(2 Suppl 1):S57-107 (2007).

Anthony et al., "Novel roles for the IgG Fc glycan," Ann N Y Acad Sci. 1253(2012):170-80 (2012).

Extended European Search Report for European Application No. 14798473.6, dated Oct. 13, 2016 (10 pages).

Anumula, "Advances in fluorescence derivatization methods for high-performance liquid chromatographic analysis of glycoprotein carbohydrates," Anal. Biochem, 2006, 350(1):1-23.

Bongers et al., "Characterization of glycosylation sites for a recombinant IgG1 monoclonal antibody and a CTLA4-Ig fusion protein by liquid chromatography-mass spectrometry peptide mapping," J. Chrom A, Nov. 2011, 1218: 8140-49.

European Office Action in Application No. 13878846.8, dated Dec. 11, 2017, 4 pages.

Hara et al., "Highly sensitive determination of N-acetyl- and N-glycolylneuraminic acids in human serum and urine and rat serum by reversed-phase liquid chromatography with fluorescence detection," J Chromatogr, Apr. 1996, 377: 111-119.

Ivancic et al., "LC/MS analysis of complex multiglycosylated human alpha(1)-acid glycoprotein as a model for developing identification and quantitation methods for intact glycopeptide analysis," Anal. Biochem, May 2010, 400: 25-32.

Larsen et al., "Rational development of LEA29Y (belatacept), a high-affinity variant of CTLA4-Ig with potent immunosuppressive properties," American Journal of Transplantation, Mar. 2005, 5:443-453.

Royle et al., "Detailed structural analysis of N-glycans released from glycoproteins in SDS-PAGE gel bands using HPLC combined with exoglycosidase array digestions," Methods Mol, Biol., 2006, 347: 125-43.

Takahashi, "Three-dimensional mapping of N-linked oligosaccharides using anion-exchange, hydrophobic and hydrophilic interaction modes of high-performance liquid chromatography," J. Chrom. A, Jan. 1996, 720: 217-25.

Varki and Diaz, "The release and purification of sialic acids from glycoconjugates: methods to minimize the loss and migration of O-acetyl groups," Anal. Biochem, Feb. 1984, 137: 236-247.

International Search Report and Written Opinion for International Patent Application No. PCT/US2013/043786, dated Jul. 3, 2014 (22 pages).

\* cited by examiner

Abatacept amino acid sequence (SEQ ID NO:1):

MHVAQPAVVLASSRGIASFVCEYASPGKATEVRVTVLRQADSQVTEVCAATYMMGNELTFLD
DSICTGTSSGNQVNLTIQGLRAMDTGLYICKVELMYPPPYYLGIGNGTQIYVIDPEPCPDSD
QEPKSSDKTHTSPPSPAPELLGGSSVFLFPPKPKDTLMISRTPEVTCVVVDVSHEDPEVKFN
WYVDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

METHODS RELATED TO CTLA4-FC FUSION PROTEINS

This disclosure provides compositions and methods related to CTLA4-Fc fusion proteins (e.g., abatacept).

REFERENCE TO A SEQUENCE LISTING

This application contains a Sequence Listing in computer readable form. The computer readable form is incorporated herein by reference.

BACKGROUND

Abatacept (marketed under the trade name ORENCIA® in both the United States and Europe) is a genetically engineered fusion protein composed of a modified Fc region of the immunoglobulin IgG1 fused to the extracellular domain of cytotoxic T-lymphocyte-associated antigen 4 (CTLA-4). Abatacept has an approximate molecular weight of 92,300 Daltons, as determined by mass spectrometry, and has a binding affinity for CD80 of approximately 6.5 nM and for CD86 of approximately 14 nM (see, Larsen et al., American Journal of Transplantation, 5:443-453 (2005)).

Abatacept is produced by mammalian cell (Chinese Hamster Ovary) culture in a nutrient medium. For intravenous administration, abatacept is supplied as a 250 mg lyophilized powder in single-use vial for reconstitution with 10 mL of sterile water. The reconstituted abatacept solution is further diluted to 100 mL by replacing a volume of 0.9% Sodium Chloride Injection, USP, with an equal volume of reconstituted abatacept solution, as required for a patient dose (see ORENCIA® Product Label). For subcutaneous administration, abatacept is supplied as a 125 mg/mL single-dose prefilled glass syringe.

SUMMARY OF THE INVENTION

The present disclosure provides, in part, methods for evaluating, identifying, and/or producing (e.g., manufacturing) a CTLA4-Fc fusion protein, e.g., abatacept. In some instances, methods herein allow highly resolved evaluation of abatacept useful for, inter alia, manufacturing abatacept, characterizing abatacept, identifying and/or confirming abatacept, monitoring the structure of abatacept, comparing abatacept preparations made over time or made under different conditions, and/or controlling the structure of abatacept.

In the first aspect, the invention features a method of manufacturing a pharmaceutical product. This method includes a CTLA4-Fc fusion protein, including: providing a sample of a test biologic preparation including a CTLA4-Fc fusion protein having an amino acid sequence with at least 95%, 98%, 99%, or 100% identity to SEQ ID NO:1, wherein amino acid 29 is alanine and amino acid 104 is leucine; acquiring an input value for each of one or more parameters in the test biologic preparation listed in Table 1; and processing the test biologic preparation into a pharmaceutical product including the CTLA4-Fc fusion protein if the input value(s) for the one or more parameters in the test biologic preparation listed in Table 1 meets the corresponding reference criterion for the parameter, thereby manufacturing a pharmaceutical product including a CTLA4-Fc fusion protein.

In a further aspect, the invention features another method of manufacturing a pharmaceutical product including a CTLA4-Fc fusion protein. This method includes: providing a host cell that is genetically engineered to express a CTLA4-Fc fusion protein having an amino acid sequence with at least about 95% identity to SEQ ID NO:1 (e.g., 95%, 98%, 99%, or 100% identity to SEQ ID NO:1), wherein amino acid 29 is alanine and amino acid 104 is leucine; culturing the host cell under conditions whereby the cell expresses the CTLA4-Fc fusion protein; harvesting the CTLA4-Fc fusion protein from the host cell culture to produce a test biologic preparation; acquiring a value for one or more parameters listed in Table 1 for the test biologic preparation; and processing at least a portion of the test biologic preparation into a pharmaceutical product including the CTLA4-Fc fusion protein if the input values for the one or more parameters in the test biologic preparation listed in Table 1 meets the corresponding reference criterion for the parameter, thereby manufacturing a pharmaceutical product including a CTLA4-Fc fusion protein.

In another aspect, the invention features yet another method of manufacturing a pharmaceutical product including a CTLA4-Fc fusion protein. This method includes: providing a host cell that is genetically engineered to express a CTLA4-Fc fusion protein having an amino acid sequence with 100% identity to SEQ ID NO: 1; culturing the host cell under conditions whereby the cell expresses the CTLA4-Fc fusion protein; harvesting the CTLA4-Fc fusion protein from the host cell culture to produce a test biologic preparation; and processing or directing the processing of at least a portion of the test biologic preparation as a pharmaceutical product including the CTLA4-Fc fusion protein if the input values for the one or more parameters in the test biologic preparation listed in Table 1 meets the reference criterion for the parameter, thereby manufacturing a pharmaceutical product including a CTLA4-Fc fusion protein.

In another aspect, the invention features a method of manufacturing a pharmaceutical product including a CTLA4-Fc fusion protein. This method includes: providing a sample of a test biologic preparation including a CTLA4-Fc fusion protein having an amino acid sequence with at least 95%, 98%, 99%, or 100% identity to SEQ ID NO:1, wherein amino acid 29 is alanine and amino acid 104 is leucine; acquiring an input value for each of one or more parameters in the test biologic preparation listed in Table 1; and processing the test biologic preparation into a pharmaceutical product including the CTLA4-Fc fusion protein if the input value(s) for at least one parameter in the test biologic preparation listed in Table 1 meets the corresponding reference criterion for the parameter, thereby manufacturing a pharmaceutical product including a CTLA4-Fc fusion protein.

In a further aspect, the invention features a method of manufacturing a pharmaceutical product including a CTLA4-Fc fusion protein. This method includes: providing a sample of a test biologic preparation including a CTLA4-Fc fusion protein having an amino acid sequence with at least 95%, 98%, 99%, or 100% identity to SEQ ID NO:1; confirming that amino acid 29 is alanine and amino acid 104 is leucine; acquiring an input value for each of one or more parameters in the test biologic preparation listed in Table 1; and processing the test biologic preparation into a pharmaceutical product including the a CTLA4-Fc fusion protein if the input value(s) for at least one parameter in the test biologic preparation listed in Table 1 meets the corresponding reference criterion for the parameter, thereby manufacturing a pharmaceutical product including a CTLA4-Fc fusion protein.

In another aspect, the invention features a method of manufacturing a pharmaceutical product including a CTLA4-Fc fusion protein. This method includes: providing a sample of a test biologic preparation including a CTLA4-Fc fusion protein having an amino acid sequence with at least 95%, 98%, 99%, or 100% identity to SEQ ID NO:1; confirming that amino acid 29 is not tyrosine and amino acid 104 is not glutamic acid; acquiring an input value for each of one or more parameters in the test biologic preparation listed in Table 1; and processing the test biologic preparation into a pharmaceutical product including the CTLA4-Fc fusion protein if the input value(s) for at least one parameter in the test biologic preparation listed in Table 1 meets the corresponding reference criterion for the parameter, thereby manufacturing a pharmaceutical product including a CTLA4-Fc fusion protein.

In a further aspect, the invention features a method of manufacturing a pharmaceutical product including a CTLA4-Fc fusion protein. This method includes: providing a sample of a test biologic preparation including a CTLA4-Fc fusion protein having an amino acid sequence with at least 95%, 98%, 99%, or 100% identity to SEQ ID NO:1; confirming that, in the CTLA4-Fc fusion protein, amino acid 29 is tyrosine and amino acid 104 is glutamic acid; acquiring an input value for each of one or more parameters in the test biologic preparation listed in Table 1; and processing the test biologic preparation into a pharmaceutical product including CTLA4-Fc fusion protein if the input value(s) for at least one parameter in the test biologic preparation listed in Table 1 meets the corresponding reference criterion for the parameter, thereby manufacturing a pharmaceutical product including a CTLA4-Fc fusion protein.

In another aspect, the invention features a method of manufacturing a pharmaceutical product including a CTLA4-Fc fusion protein. This method including: providing a sample of a test biologic preparation including a CTLA4-Fc fusion protein having an amino acid sequence with at least 95%, 98%, 99%, or 100% identity to SEQ ID NO:1; confirming that amino acid 29 is alanine and amino acid 104 is leucine; acquiring an input value for each of one or more parameters in the test biologic preparation listed in Table 1; and processing the test biologic preparation into a pharmaceutical product including the a CTLA4-Fc fusion protein if the input value(s) for the one or more parameters in the test biologic preparation listed in Table 1 meets the corresponding reference criterion for the parameter, thereby manufacturing a pharmaceutical product including a CTLA4-Fc fusion protein.

In a further aspect, the invention features a method of manufacturing a pharmaceutical product including a CTLA4-Fc fusion protein. This method includes: providing a sample of a test biologic preparation including a CTLA4-Fc fusion protein having an amino acid sequence with at least 95%, 98%, 99%, or 100% identity to SEQ ID NO:1; confirming that amino acid 29 is not tyrosine and amino acid 104 is not glutamic acid; acquiring an input value for each of one or more parameters in the test biologic preparation listed in Table 1; and processing the test biologic preparation into a pharmaceutical product including the CTLA4-Fc fusion protein if the input value(s) for the one or more parameters in the test biologic preparation listed in Table 1 meets the corresponding reference criterion for the parameter, thereby manufacturing a pharmaceutical product including a CTLA4-Fc fusion protein.

In another aspect, the invention features a method of manufacturing a pharmaceutical product including a CTLA4-Fc fusion protein. This method includes: providing a sample of a test biologic preparation including a CTLA4-Fc fusion protein having an amino acid sequence with at least 95%, 98%, 99%, or 100% identity to SEQ ID NO:1; confirming that, in the CTLA4-Fc fusion protein, amino acid 29 is tyrosine and amino acid 104 is glutamic acid; acquiring an input value for each of one or more parameters in the test biologic preparation listed in Table 1; and processing the test biologic preparation into a pharmaceutical product including CTLA4-Fc fusion protein if the input value(s) for the one or more parameters in the test biologic preparation listed in Table 1 meets the corresponding reference criterion for the parameter, thereby manufacturing a pharmaceutical product including a CTLA4-Fc fusion protein.

In certain embodiments, any of the foregoing methods also include after the step of acquiring the input value(s) and before the step of processing, acquiring one or more assessments made by comparing the input value with one or more target values for a target biologic having a first amino acid sequence with 100% identity to SEQ ID NO:1, wherein the target biologic is approved under a BLA or a supplemental BLA.

In other embodiments of any of the foregoing methods, the processed biologic is approved under Section 351(k) of the Public Health Service (PHS) Act.

In further embodiments of any of the foregoing methods, the processed biologic is not approved under a BLA under Section 351(a) of the PHS Act.

In further embodiments of any of the foregoing methods, the processed biologic is approved under a BLA under Section 351(a) of the PHS Act.

In some embodiments of any of the foregoing methods, the input value is acquired for one, two, or more samples or batches.

In still further embodiments of any of the foregoing methods, the value for the test biologic preparation comprises an average (e.g., mean) of a range of values for the parameter for multiple (e.g., 2, 3, 4, 5, 10, 15, 20, or more) batches or samples of the test biologic.

In some embodiments of any of the foregoing methods, one or more, including all, of the reference criteria shown in Table 1 is/are a specification for commercial release of a drug product under Section 351(k) of the PHS Act.

In another aspect, the invention features a method of manufacturing abatacept, including: providing or obtaining a test biologic preparation; acquiring an input value for one or more parameters listed in Table 1 for the test biologic preparation; and processing at least a portion of the test biologic preparation into a pharmaceutical product if the input values for the one or more parameters in the test biologic preparation listed in Table 1 meets the corresponding reference criterion for the parameter, thereby manufacturing abatacept.

In some embodiments, any of the foregoing methods include acquiring input values for any combination of two or more parameters listed in Table 1.

In a further embodiment, any of the foregoing methods include acquiring an input value for a plurality of parameters listed in Table 1.

In a still further embodiment, the test biologic preparation has an amino acid sequence with 100% identity to SEQ ID NO:1.

In yet other embodiments of any of the foregoing methods, the method includes, after the step of acquiring the value(s) and before the step of processing, obtaining a plurality of assessments made by comparing the value(s) with a corresponding reference criterion shown in Table 1.

In further embodiments of any of the foregoing methods, at least one value is directly obtained by performing an analytical test on the test biologic preparation.

In other embodiments of any of the foregoing methods, the value is directly obtained using a method provided in Table 7.

In still other embodiments of any of the foregoing methods, the processing step comprises combining the test biologic preparation with an excipient or buffer.

In some embodiments of any of the foregoing methods, the processing step includes one or more of: formulating the test biologic preparation; processing the test biologic preparation into a drug product; combining the test biologic preparation with a second component, e.g., an excipient or buffer; changing the concentration of the biologic in the preparation; lyophilizing the test biologic preparation; combining a first and second aliquot of the biologic to provide a third, larger, aliquot; dividing the test biologic preparation into smaller aliquots; disposing the test biologic preparation into a container, e.g., a gas or liquid tight container; packaging the test biologic preparation; associating a container including the test biologic preparation with a label (e.g., labeling); and shipping or moving the test biologic to a different location.

In another aspect, the disclosure features methods for high resolution and site-specific deconvolution of glycan profiles for glycoproteins having multiple (e.g., two or more) glycosylation sites. In some instances, methods includes the steps of: (a) providing a test biologic preparation that includes one or more N- and/or O-glycans; (b) digesting the test biologic preparation with one or more protease enzymes (e.g., including, but not limited to, Arg-C endoproteinase, trypsin, chymo-trypsin, Asp-N endopeptidase, Glu-C endoproteinase, Lys-C endoproteinase) in a digestion buffer that is compatible with mass spectrometry, wherein the digestion is optionally performed using pressure cycling technology under conditions sufficient to allow at least 75% digestion of the protein into constituent peptides in a time of under 5 hours; in some instances so as to minimize sample prep induced modifications of the amino acid backbone (e.g. deamidation, methionine oxidation); (c) separating the digested test biologic preparation to produce two or more separated components of the test biologic preparation; and (d) determining the identity, location, and/or abundance of one or more N- and/or O-linked glycans in one or more of the separated components.

In one embodiment, the test biologic preparation includes a biologic having an amino acid sequence with at least 95% identity (e.g., 95%, 96%, 97%, 98%, 99%, wherein amino acid 29 is alanine and amino acid 104 is leucine or 100% identity) to SEQ ID NO:1. In another embodiment, the test biologic preparation includes a biologic having an amino acid sequence with 100% identity to SEQ ID NO:1.

In one embodiment, the digesting and separating steps permit the separation of a first component containing Ser129 from a second component containing Ser139. In another embodiment, the digesting and separating steps permit the separation of the following into distinct components: a component containing O-linked site Ser129; a component containing Asn207; a component containing major non-glycopeptides; a component containing Ser139; a component containing Asn108; and a component containing Asn76.

In certain embodiments of any of the above methods, the one or more parameters in the test biologic preparation include parameter 1. In other embodiments, the one or more parameters in the test biologic preparation include parameter 2. In other embodiments, the one or more parameters in the test biologic preparation include parameter 3. In other embodiments, the one or more parameters in the test biologic preparation include parameter 4. In other embodiments, the one or more parameters in the test biologic preparation include parameter 5. In other embodiments, the one or more parameters in the test biologic preparation include parameter 6. In other embodiments, the one or more parameters in the test biologic preparation include parameter 7. In other embodiments, the one or more parameters in the test biologic preparation include parameter 8. In other embodiments, the one or more parameters in the test biologic preparation include parameter 9. In other embodiments, the one or more parameters in the test biologic preparation include parameter 10. In other embodiments, the one or more parameters in the test biologic preparation include parameter 11. In other embodiments, the one or more parameters in the test biologic preparation include parameter 12. In other embodiments, the one or more parameters in the test biologic preparation include parameter 13. In other embodiments, the one or more parameters in the test biologic preparation include parameter 14. In other embodiments, the one or more parameters in the test biologic preparation include parameter 15. In other embodiments, the one or more parameters in the test biologic preparation include parameter 16. In other embodiments, the one or more parameters in the test biologic preparation include parameter 17. In other embodiments, the one or more parameters in the test biologic preparation include parameter 18. In other embodiments, the one or more parameters in the test biologic preparation include parameter 19. In other embodiments, the one or more parameters in the test biologic preparation include parameter 20. In other embodiments, the one or more parameters in the test biologic preparation include parameter 21. In other embodiments, the one or more parameters in the test biologic preparation include parameter 22. In other embodiments, the one or more parameters in the test biologic preparation include parameter 23. In other embodiments, the one or more parameters in the test biologic preparation include parameter 24. In other embodiments, the one or more parameters in the test biologic preparation include parameter 25. In other embodiments, the one or more parameters in the test biologic preparation include parameter 26. In other embodiments, the one or more parameters in the test biologic preparation include parameter 27. In other embodiments, the one or more parameters in the test biologic preparation include parameter 28. In other embodiments, the one or more parameters in the test biologic preparation include parameter 29. In other embodiments, the one or more parameters in the test biologic preparation include parameter 30. In other embodiments, the one or more parameters in the test biologic preparation include parameter 31. In other embodiments, the one or more parameters in the test biologic preparation include parameter 32. In other embodiments, the one or more parameters in the test biologic preparation include parameter 33. In other embodiments, the one or more parameters in the test biologic preparation include parameter 34. In other embodiments, the one or more parameters in the test biologic preparation include parameter 35. In other embodiments, the one or more parameters in the test biologic preparation include parameter 36. In other embodiments, the one or more parameters in the test biologic preparation include parameter 37. In other embodiments, the one or more parameters in the test biologic preparation include parameter 38. In other embodiments, the one or more parameters in the test biologic preparation include parameter 39. In other embodiments, the one or more parameters in the test biologic preparation include parameter 40. In other embodiments, the one or more parameters in the test biologic preparation include parameter 41. In other embodiments, the one or more parameters in the test biologic preparation include parameter 42. In other embodiments, the one or more parameters in the test biologic preparation include parameter 43. In other embodiments, the one or more parameters in the test biologic preparation include parameter 44. In other embodiments, the one or more parameters in the test biologic preparation include parameter 45. In other embodiments, the one or more parameters in the test biologic preparation include parameter 46. In other embodiments, the one or more parameters in the test biologic preparation include parameter 47. In other embodiments, the one or more parameters in the test biologic preparation include parameter 48. In other embodiments, the one or more parameters in the test biologic preparation include parameter 49. In other embodiments, the one or more parameters in the test biologic preparation include parameter 50. In other embodiments, the one or more parameters in the test biologic preparation include parameter 51. In other embodiments, the one or more parameters in the test biologic preparation include parameter 52. In other embodiments, the one or more parameters in the test biologic preparation include parameter 53. In other embodiments, the one or more parameters in the test biologic preparation include parameter 54.

In other embodiments of any of the above methods, the one or more parameters in the test biologic preparation do not include parameter 1. In other embodiments, the one or more parameters in the test biologic preparation do not include parameter 2. In other embodiments, the one or more parameters in the test biologic preparation do not include parameter 3. In other embodiments, the one or more parameters in the test biologic preparation do not include parameter 4. In other embodiments, the one or more parameters in the test biologic preparation do not include parameter 5. In other embodiments, the one or more parameters in the test biologic preparation do not include parameter 6. In other embodiments, the one or more parameters in the test biologic preparation do not include parameter 7. In other embodiments, the one or more parameters in the test biologic preparation do not include parameter 8. In other embodiments, the one or more parameters in the test biologic preparation do not include parameter 9. In other embodiments, the one or more parameters in the test biologic preparation do not include parameter 10. In other embodiments, the one or more parameters in the test biologic preparation do not include parameter 11. In other embodiments, the one or more parameters in the test biologic preparation do not include parameter 12. In other embodiments, the one or more parameters in the test biologic preparation do not include parameter 13. In other embodiments, the one or more parameters in the test biologic preparation do not include parameter 14. In other embodiments, the one or more parameters in the test biologic preparation do not include parameter 15. In other embodiments, the one or more parameters in the test biologic preparation do not include parameter 16. In other embodiments, the one or more parameters in the test biologic preparation do not include parameter 17. In other embodiments, the one or more parameters in the test biologic preparation do not include parameter 18. In other embodiments, the one or more parameters in the test biologic preparation do not include parameter 19. In other embodiments, the one or more parameters in the test biologic preparation do not include parameter 20. In other embodiments, the one or more parameters in the test biologic preparation do not include parameter 21. In other embodiments, the one or more parameters in the test biologic preparation do not include parameter 22. In other embodiments, the one or more parameters in the test biologic preparation do not include parameter 23. In other embodiments, the one or more parameters in the test biologic preparation do not include parameter 24. In other embodiments, the one or more parameters in the test biologic preparation do not include parameter 25. In other embodiments, the one or more parameters in the test biologic preparation do not include parameter 26. In other embodiments, the one or more parameters in the test biologic preparation do not include parameter 27. In other embodiments, the one or more parameters in the test biologic preparation do not include parameter 28. In other embodiments, the one or more parameters in the test biologic preparation do not include parameter 29. In other embodiments, the one or more parameters in the test biologic preparation do not include parameter 30. In other embodiments, the one or more parameters in the test biologic preparation do not include parameter 31. In other embodiments, the one or more parameters in the test biologic preparation do not include parameter 32. In other embodiments, the one or more parameters in the test biologic preparation do not include parameter 33. In other embodiments, the one or more parameters in the test biologic preparation do not include parameter 34. In other embodiments, the one or more parameters in the test biologic preparation do not include parameter 35. In other embodiments, the one or more parameters in the test biologic preparation do not include parameter 36. In other embodiments, the one or more parameters in the test biologic preparation do not include parameter 37. In other embodiments, the one or more parameters in the test biologic preparation do not include parameter 38. In other embodiments, the one or more parameters in the test biologic preparation do not include parameter 39. In other embodiments, the one or more parameters in the test biologic preparation do not include parameter 40. In other embodiments, the one or more parameters in the test biologic preparation do not include parameter 41. In other embodiments, the one or more parameters in the test biologic preparation do not include parameter 42. In other embodiments, the one or more parameters in the test biologic preparation do not include parameter 43. In other embodiments, the one or more parameters in the test biologic preparation do not include parameter 44. In other embodiments, the one or more parameters in the test biologic preparation do not include parameter 45. In other embodiments, the one or more parameters in the test biologic preparation do not include parameter 46. In other embodiments, the one or more parameters in the test biologic preparation do not include parameter 47. In other embodiments, the one or more parameters in the test biologic preparation do not include parameter 48. In other embodiments, the one or more parameters in the test biologic preparation do not include parameter 49. In other embodiments, the one or more parameters in the test biologic preparation do not include parameter 50. In other embodiments, the one or more parameters in the test biologic preparation do not include parameter 51. In other embodiments, the one or more parameters in the test biologic preparation do not include parameter 52. In other embodiments, the one or more parameters in the test biologic preparation do not include parameter 53. In other embodiments, the one or more parameters in the test biologic preparation do not include parameter 54.

In still other embodiments of any of the above methods, the one or more parameters in the test biologic preparation include a parameter present at N108 (parameters 2, 7, 17, 20, 22, 23, 25, 33, 34, 37, and 40). In other embodiments, the one or more parameters in the test biologic preparation include a parameter present at N76 (parameters 1, 6, 16, 19, 21, 27, 32, 34, 36, and 39). In other embodiments, the one or more parameters in the test biologic preparation include a parameter present at N207 (parameters 5, 10, 15, 18, 24, 26, 29-31, and 38). In other embodiments, the one or more parameters in the test biologic preparation include a parameter at present O129 (parameters 3, 8, 41, and 42). In other embodiments, the one or more parameters in the test biologic preparation include a parameter at present O139 (parameters 4, 9, and 44-46). In other embodiments, the one or more parameters in the test biologic preparation include a parameter pertaining to the structure of one or more glycans (parameters 5-10, 15-46, and 52-54). In other embodiments, the one or more parameters in the test biologic preparation include a parameter pertaining to the location of one or more glycans (parameters 1-10 and 15-46). In other embodiments, the one or more parameters in the test biologic preparation include a parameter pertaining to the abundance of one or more glycans (parameters 15-46, and 52-54). In other embodiments, the one or more parameters in the test biologic preparation include a parameter pertaining to the amount of lysine at the C-terminus (parameter 11). In other embodiments, the one or more parameters in the test biologic preparation include a parameter pertaining to the charge distribution of the glycans (parameters 49-51). In other embodiments, the one or more parameters in the test biologic preparation include a parameter pertaining to the number of different glycans (parameters 1-5). In other embodiments, the one or more parameters in the test biologic preparation include a parameter pertaining to the amount of post-translational glycation (parameters 12-14). In other embodiments, the one or more parameters in the test biologic preparation include a parameter pertaining to the abundance of NeuGC (parameters 15-20). In other embodiments, the one or more parameters in the test biologic preparation include a parameter pertaining to the amount of post-translational sulfation (parameters 21-22). In other embodiments, the one or more parameters in the test biologic preparation include a parameter pertaining to the amount of post-translational acylation (parameters 23-27). In certain embodiments, the one or more parameters in the test biologic preparation include a parameter pertaining to the structure, location, or abundance of a glycan (parameters 1-10, 15-46, and 52-54).

In still other embodiments of any of the above methods, the one or more parameters in the test biologic preparation do not include a parameter present at N108 (parameters 2, 7, 17, 20, 22, 23, 25, 33, 34, 37, and 40). In other embodiments, the one or more parameters in the test biologic preparation do not include a parameter present at N76 (parameters 1, 6, 16, 19, 21, 27, 32, 34, 36, and 39). In other embodiments, the one or more parameters in the test biologic preparation do not include a parameter present at N207 (parameters 5, 10, 15, 18, 24, 26, 29-31, and 38). In other embodiments, the one or more parameters in the test biologic preparation do not include a parameter at present O129 (parameters 3, 8, 41, and 42). In other embodiments, the one or more parameters in the test biologic preparation do not include a parameter at present O139 (parameters 4, 9, and 44-46). In other embodiments, the one or more parameters in the test biologic preparation do not include a parameter pertaining to the structure of one or more glycans (parameters 5-10, 15-46, and 52-54). In other embodiments, the one or more parameters in the test biologic preparation do not include a parameter pertaining to the location of one or more glycans (parameters 1-10 and 15-46). In other embodiments, the one or more parameters in the test biologic preparation do not include a parameter pertaining to the abundance of one or more glycans (parameters 15-46, and 52-54). In other embodiments, the one or more parameters in the test biologic preparation do not include a parameter pertaining to the amount of lysine at the C-terminus (parameter 11). In other embodiments, the one or more parameters in the test biologic preparation do not include a parameter pertaining to the charge distribution of the glycans (parameters 49-51). In other embodiments, the one or more parameters in the test biologic preparation do not include a parameter pertaining to the number of different glycans (parameters 1-5). In other embodiments, the one or more parameters in the test biologic preparation do not include a parameter pertaining to the amount of post-translational glycation (parameters 12-14). In other embodiments, the one or more parameters in the test biologic preparation do not include a parameter pertaining to the abundance of NeuGC (parameters 15-20). In other embodiments, the one or more parameters in the test biologic preparation do not include a parameter pertaining to the amount of post-translational sulfation (parameters 21-22). In other embodiments, the one or more parameters in the test biologic preparation do not include a parameter pertaining to the amount of post-translational acylation (parameters 23-27). In certain embodiments, the one or more parameters in the test biologic preparation do not include a parameter pertaining to the structure, location, or abundance of a glycan (parameters 1-10, 15-46, and 52-54).

In certain embodiments, the combination of two or more parameters in the test biologic preparation include a parameter pertaining to the structure, location, or abundance of a glycan (parameters 1-10, 12-46, and 52-54) and a parameter pertaining to the amount of lysine at the C-terminus (parameter 11). In certain embodiments, the combination of two or more parameters in the test biologic preparation include a parameter pertaining to the structure, location, or abundance of a glycan (parameters 1-10, 12-46, and 52-54) and a parameter pertaining to the charge distribution of the glycans (parameters 49-51). In certain embodiments, the combination of two or more parameters in the test biologic preparation include a parameter pertaining to the structure, location, or abundance of a glycan (parameters 1-10, 12-46, and 52-54) and a parameter pertaining to the amount of post-translational glycation (parameters 12-14). In certain embodiments, the combination of two or more parameters in the test biologic preparation include a parameter pertaining to the charge distribution of the glycans (parameters 47-51) and a parameter pertaining to the amount of lysine at the C-terminus (parameter 11). In certain embodiments, the combination of two or more parameters in the test biologic preparation include a parameter pertaining to the charge distribution of the glycans (parameters 47-51) and a parameter pertaining to the amount of post-translational glycation (parameters 12-14). In certain embodiments, the combination of two or more parameters in the test biologic preparation include a parameter pertaining to the amount of lysine at the C-terminus (parameter 11) and a parameter pertaining to the amount of post-translational glycation (parameters 12-14). In certain embodiments, the combination of two or more parameters in the test biologic preparation include a parameter pertaining to the structure, location, or abundance of a glycan (parameters 1-10, 12-46, and 52-54), a parameter pertaining to the charge distribution of the glycans (parameters 47-51), and a parameter pertaining to the amount of lysine at the C-terminus (parameter 11). In certain embodiments, the combination of two or more parameters in the test biologic preparation include a parameter pertaining to the structure, location, or abundance of a glycan (parameters 1-10, 12-46, and 52-54), a parameter pertaining to the charge distribution of the glycans (parameters 47-51), and a parameter pertaining to the amount of post-translational glycation (parameters 12-14). In certain embodiments, the combination of two or more parameters in the test biologic preparation include a parameter pertaining to the structure, location, or abundance of a glycan (parameters 1-10, 12-46, and 52-54), a parameter pertaining to the amount of post-translational glycation (parameters 12-14), and a parameter pertaining to the amount of lysine at the C-terminus (parameter 11). In certain embodiments, the combination of two or more parameters in the test biologic preparation include a parameter pertaining to the charge distribution of the glycans (parameters 47-51), a parameter pertaining to the amount of post-translational glycation (parameters 12-14), and a parameter pertaining to the amount of lysine at the C-terminus (parameter 11). In certain embodiments, the combination of two or more parameters in the test biologic preparation include a parameter pertaining to the structure, location, or abundance of a glycan (parameters 1-10, 12-46, and 52-54), a parameter pertaining to the charge distribution of the glycans (parameters 47-51), a parameter pertaining to the amount of post-translational glycation (parameters 12-14), and a parameter pertaining to the amount of lysine at the C-terminus (parameter 11).

In still other embodiments of any of the above methods, a combination of two parameters are compared to the reference criteria. In other embodiments, a combination of three parameters are compared to the reference criteria. In other embodiments, a combination of four parameters are compared to the reference criteria. In other embodiments a combination of five parameters are compared to the reference criteria. In other embodiments, a combination of six parameters are compared to the reference criteria. In other embodiments, a combination of seven parameters are compared to the reference criteria. In other embodiments, a combination of eight parameters are compared to the reference criteria. In other embodiments, a combination of nine parameters are compared to the reference criteria. In other embodiments, a combination of ten parameters are compared to the reference criteria. In other embodiments, a combination of 11 parameters are compared to the reference criteria. In other embodiments, a combination of 12 parameters are compared to the reference criteria. In other embodiments, a combination of 13 parameters are compared to the reference criteria. In other embodiments, a combination of 14 parameters are compared to the reference criteria. In other embodiments, a combination of 15 parameters are compared to the reference criteria. In other embodiments, a combination of 16 parameters are compared to the reference criteria. In other embodiments, a combination of 17 parameters are compared to the reference criteria. In other embodiments, a combination of 18 parameters are compared to the reference criteria. In other embodiments, a combination of 19 parameters are compared to the reference criteria. In other embodiments, a combination of 20 parameters are compared to the reference criteria. In other embodiments, a combination of 21 parameters are compared to the reference criteria. In other embodiments, a combination of 22 parameters are compared to the reference criteria. In other embodiments, a combination of 23 parameters are compared to the reference criteria. In other embodiments, a combination of 24 parameters are compared to the reference criteria. In other embodiments, a combination of 25 parameters are compared to the reference criteria. In other embodiments, a combination of 26 parameters are compared to the reference criteria. In other embodiments, a combination of 27 parameters are compared to the reference criteria. In other embodiments, a combination of 28 parameters are compared to the reference criteria. In other embodiments, a combination of 29 parameters are compared to the reference criteria. In other embodiments, a combination of 30 parameters are compared to the reference criteria. In other embodiments, a combination of 31 parameters are compared to the reference criteria. In other embodiments, a combination of 32 parameters are compared to the reference criteria. In other embodiments, a combination of 33 parameters are compared to the reference criteria. In other embodiments, a combination of 34 parameters are compared to the reference criteria. In other embodiments, a combination of 35 parameters are compared to the reference criteria. In other embodiments, a combination of 36 parameters are compared to the reference criteria. In other embodiments, a combination of 37 parameters are compared to the reference criteria. In other embodiments, a combination of 38 parameters are compared to the reference criteria. In other embodiments, a combination of 39 parameters are compared to the reference criteria. In other embodiments, a combination of 40 parameters are compared to the reference criteria. In other embodiments, a combination of 41 parameters are compared to the reference criteria. In other embodiments, a combination of 42 parameters are compared to the reference criteria. In other embodiments, a combination of 43 parameters are compared to the reference criteria. In other embodiments, a combination of 44 parameters are compared to the reference criteria. In other embodiments, a combination of 45 parameters are compared to the reference criteria. In other embodiments, a combination of 46 parameters are compared to the reference criteria. In other embodiments, a combination of 47 parameters are compared to the reference criteria. In other embodiments, a combination of 48 parameters are compared to the reference criteria. In other embodiments, a combination of 49 parameters are compared to the reference criteria. In other embodiments, a combination of 50 parameters are compared to the reference criteria. In other embodiments, a combination of 51 parameters are compared to the reference criteria. In other embodiments, a combination of 52 parameters are compared to the reference criteria. In other embodiments, a combination of 53 parameters are compared to the reference criteria. In other embodiments, a combination of 54 parameters are compared to the reference criteria.

As used herein, an abatacept signature or fingerprint comprises a plurality of reference criteria or rules for a plurality of parameters that define abatacept. In some instances, an abatacept signature can be contained in or part of a pharmaceutical specification, a commercial product release specification, a product acceptance criterion, a pharmacopeial standard, or a product labeling description. In some instances, the abatacept signature comprises a plurality of reference criteria or rules for a plurality of parameters shown in Table 1:

TABLE 1

| Parameter # | Parameter Category | Parameter Location | Parameter | Reference Criterion (rule) |
|---|---|---|---|---|
| 1 | Identified Glycans | N76 | # of different glycans identified | >11 |
| 2 | Identified Glycans | N108 | # of different glycans identified | >6 |
| 3 | Identified Glycans | O129 | # of different glycans identified | >1 |
| 4 | Identified Glycans | O139 | # of different glycans identified | >3 |
| 5 | Identified Glycans | N207 | # of different glycans identified | >14 |
| 6 | Identified Glycans | N76 | identification of one or more glycans listed in Table 2 | Detectable |
| 7 | Identified Glycans | N108 | identification of one or more glycans listed in Table 3 | Detectable |
| 8 | Identified Glycans | O129 | identification of one or more glycans listed in Table 4 | Detectable |
| 9 | Identified Glycans | O139 | identification of one or more glycans listed in Table 5 | Detectable |
| 10 | Identified Glycans | N207 | identification of one or more glycans listed in Table 6 | Detectable |
| 11 | C-terminal lysine | C-terminus | amount of lysine present at the C-terminus | <20% |
| 12 | PTM (glycation) | K198 | amount of post-translational glycation | Detectable and <2% |
| 13 | PTM (glycation) | K200 | amount of post-translational glycation | Not detectable |
| 14 | PTM (glycation) | K198 and K200 | amount of post-translational double glycation | Detectable and <2% |
| 15 | NeuGc | N207 | | 0.4-0.8% |
| 16 | NeuGc | N76 | | 1.0-1.5% |
| 17 | NeuGc | N108 | | 1.4-2.6% |
| 18 | NeuGc | N207 | | Detectable and <0.5% |
| 19 | NeuGc | N76 | | 0.4-0.9% |
| 20 | NeuGc | N108 | | Detectable and <0.5% |
| 21 | Sulfated | N76 | | 0.4-0.8% |

TABLE 1-continued

| Parameter # | Parameter Category | Parameter Location | Parameter | Reference Criterion (rule) |
|---|---|---|---|---|
| 22 | Sulfated | N108 | | Detectable and <0.5% |
| 23 | Acetylated | N108 | | 3.8-5.8% |
| 24 | Acetylated | N207 | | Detectable and <0.5% |
| 25 | Acetylated | N108 | | 1.1-2% |
| 26 | Acetylated | N207 | | Detectable and <0.5% |
| 27 | Acetylated | N76 | | 0.3-0.6% |
| 28 | Aglyco | N76 | aglyco | 2.6-4.5% |
| 29 | Aglyco | N207 | aglyco | 0.7-1.2% |
| 30 | Glycan | N207 | | 17.1-29.9% |
| 31 | Glycan | N207 | | 24.8-39.5% |
| 32 | Glycan | N76 | | 9.2-17.5% |

TABLE 1-continued
| Parameter # | Parameter Category | Parameter Location | Parameter | Reference Criterion (rule) |
|---|---|---|---|---|
| 33 | Glycan | N108 | 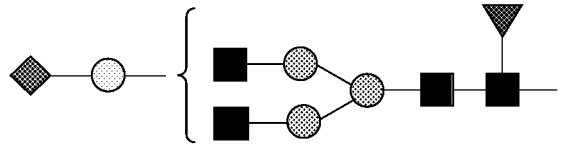 | 4.7-8.3% |
| 34 | Glycan | N76 | 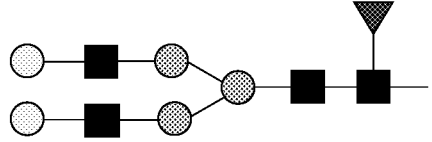 | 5.1-9.5% |
| 35 | Glycan | N108 | 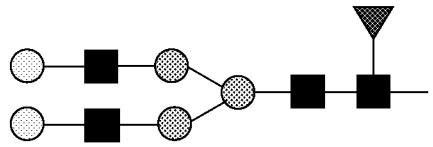 | 9.8-18.6% |
| 36 | Glycan | N76 | 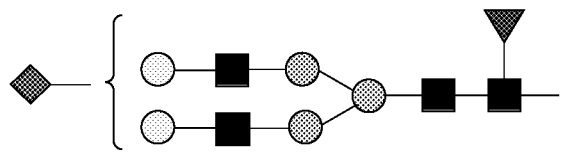 | 19.1-31.4% |
| 37 | Glycan | N108 | 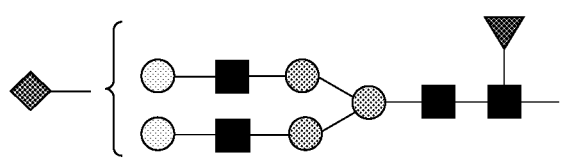 | 20.2-31.8% |
| 38 | Glycan | N207 | 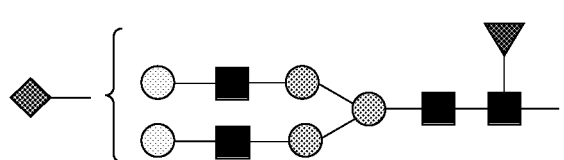 | 7.1-12.1% |
| 39 | Glycan | N76 | 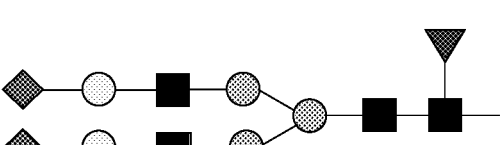 | 11.1-20.0% |
| 40 | Glycan | N108 | 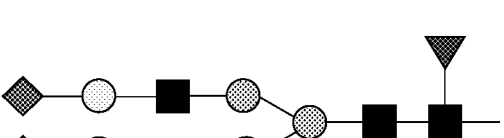 | 13.4-23.3% |
| 41 | Aglyco | O129 | aglyco | 36.2-59.3% |
| 42 | Glycan | O129 |  | 37.2-61.27% |
| 43 | Aglyco | O139 | aglyco | 0.8-2.7% |
| 44 | Glycan | O139 |  | 62.4-94.5% |

TABLE 1-continued

| Parameter # | Parameter Category | Parameter Location | Parameter | Reference Criterion (rule) |
|---|---|---|---|---|
| 45 | Glycan | O139 | 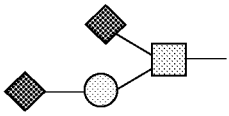 | 7.0-12.5% |
| 46 | Glycan | O139 | 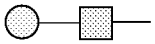 | 2.2-3.9% |
| 47 | Charged glycans | N/A | Neutral glycans | 30.2-49.3% |
| 48 | Charged glycans | N/A | Monosialylated glycans | 24.5-38.2% |
| 49 | Charged glycans | N/A | Disialylated glycans | 17.3-28.9% |
| 50 | Charged glycans | N/A | Trisialylated glycans | 2.4-4.3% |
| 51 | Charged glycans | N/A | Tetrasialylated glycans | 0.8-2.2% |
| 52 | NeuGc | N/A | Amount of sialic acid that is NeuGc | Detectable and <8% |
| 53 | Acetylated | N/A | Amount of sialic acid that contains 2 or more acetyl groups | 4-9% |
| 54 | Sulfation | N/A | % of glycans that contain one or more sulfate groups | Detectable and <4% |

For parameters 15-27, 30-40, 42, and 44-46, percent (%) refers to the number of moles of peptide containing glycan X relative to total moles of that peptide (with or without a glycan) detected as disclosed herein, wherein X represents the parameter of interest.

For parameter 11, percent (%) refers to the level of C-terminal-lysine-containing peptide relative to the sum of the levels of C-terminal-lysine-containing and C-terminal-lysine-free peptides detected as disclosed in Table 7.

For parameters 12-14, percent (%) refers to the level of glycated peptide relative to the sum of the glycated peptide and unmodified peptides detected as disclosed in Table 7.

For parameters 28-29, 41, and 43, percent (%) refers to the level of Aglyco peptide Y relative to the sum of the levels of Aglyco peptide Y and glycan-containing peptide Y, detected as disclosed in Table 7, wherein Y represents the parameter of interest.

For parameters 47-51, percent (%) refers to the number of moles of PNGase F-released glycan(s) X relative to total moles of PNGase F-released glycans detected as disclosed in Table 7, wherein X represents the parameter of interest.

For parameter 52, percent (%) refers to the number of moles of sialic acid that is NeuGc relative to total moles of sialic acid, detected as disclosed in Table 7.

For parameter 53, percent (%) refers to the number of moles of sialic acid residues containing two or more acetyle groups relative to total moles of sialic acid residues, detected as disclosed in Table 7.

For parameter 54, percent (%) refers to the number of moles of PNGase F-released glycans that contain one or more sulfate moieties relative to total moles of PNGase F-released glycans detected as disclosed in Table 7.

By "detectable" is meant that the recited parameter can be detected by one of ordinary skill using a method disclosed in Table 7 or as disclosed herein.

TABLE 2

N76 Glycan Structures

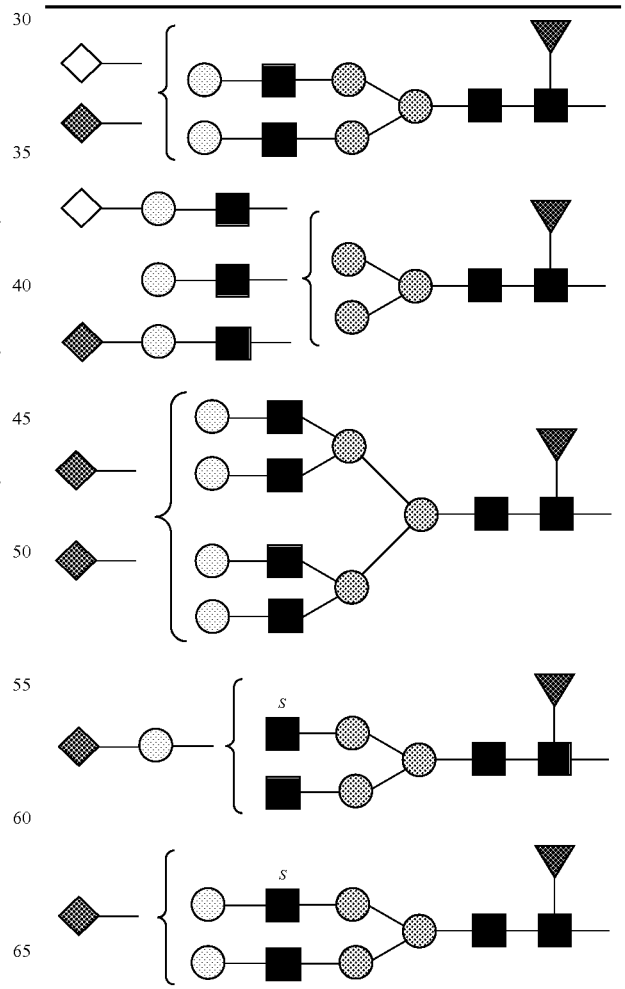

TABLE 2-continued
N76 Glycan Structures
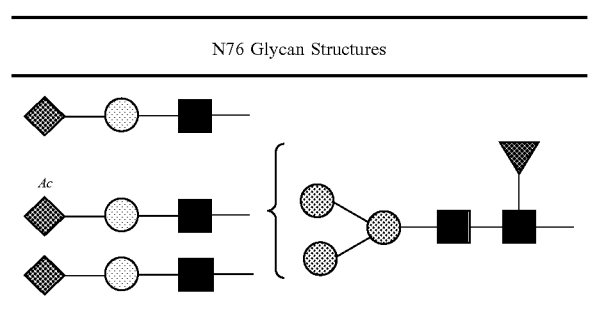
Mannose
●
Fucose
▼
GlcNAc
■
Galactose
○
NeuAc
◆
NeuGc
◇
GalNac
▫
TABLE 3
N108 Glycan Structures
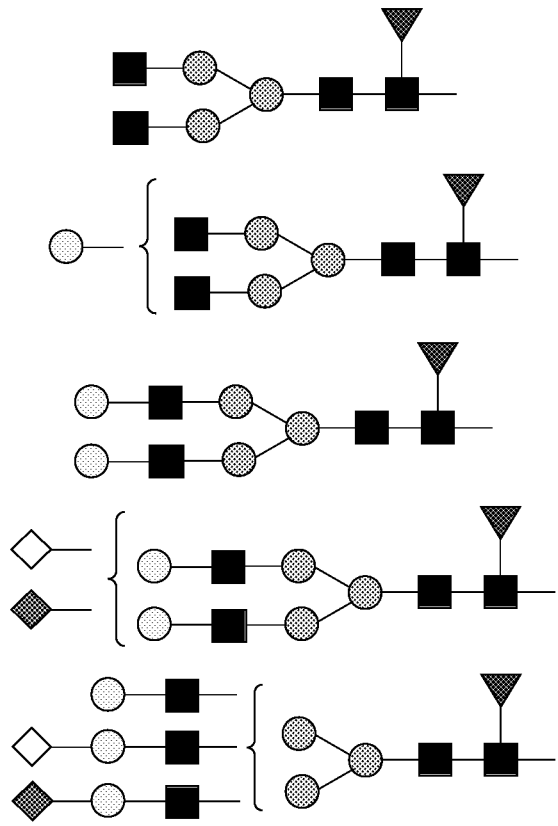
TABLE 3-continued
N108 Glycan Structures
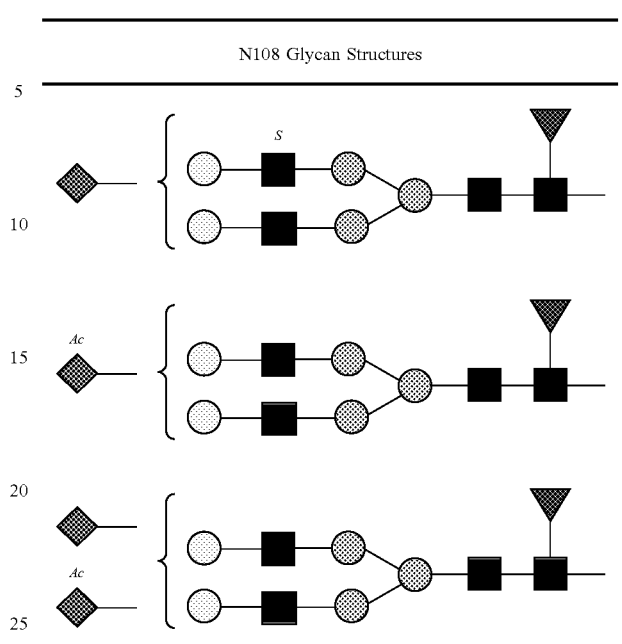
TABLE 4
O129 Glycan Structure
TABLE 5
O139 Glycan Structures
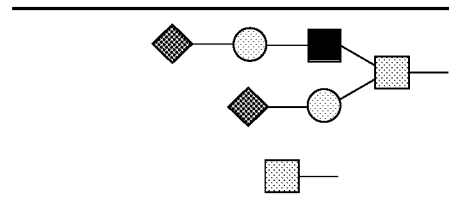
TABLE 6
N207 Glycan Structures
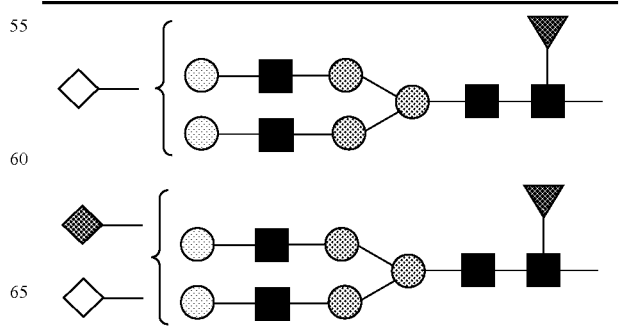

TABLE 6-continued

N207 Glycan Structures

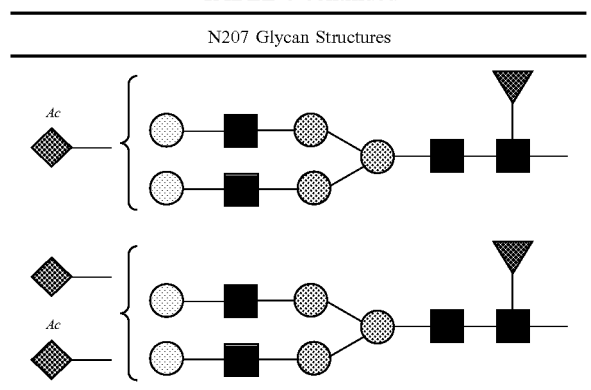

While the present disclosure provides exemplary units and methods for the evaluation, identification, and production methods disclosed herein (see, e.g., Tables 1-7), a person of ordinary skill in the art will appreciate that performance of the evaluation, identification, and production methods herein is not limited to use of those units and/or methods. For example, abatacept signatures provided herein are generally described, for certain parameters, as a value for a glycan or structure relative to total glycan or structure on a mol/mol basis (see, e.g., Table 1). A person of skill in the art understands that although the use of other metrics or units (e.g., mass/mass, mole percent vs. weight percent) to measure a described parameter might give rise to different absolute values than those described herein, e.g., in Table 1, a test biologic preparation meets a disclosed abatacept reference criterion or signature even if other units or metrics are used, as long as the test biologic preparation meets the herein disclosed reference criterion or signature when the herein disclosed units and metrics are used, e.g., allowing for the sensitivity (e.g., analytical variability) of the method being used to measure the value.

Abatacept parameters shown in Table 1 are parameters that, alone, in any combination, or together, distinguish abatacept from non-abatacept biologic (see below). In some instances, an abatacept parameter is part of the biologic, e.g., connected with the rest of the biologic by a covalent bond, i.e., an intrinsic parameter. Intrinsic parameters include the presence, absence, level, ratio (with another entity), or distribution of a physical moiety, e.g., a moiety arising from or associated with a post-translational event. Parameters of this type include the presence (or absence), abundance, absolute or relative amount, ratio (with another entity), or distribution of a glycan, a linkage, a glycoform, or post-translationally added components of the preparation. In some instances, a parameter is not part of the biologic but is present in the preparation with the biologic (i.e., in a biologic preparation), i.e., an extrinsic parameter. Exemplary parameters of this type include the presence (or absence), abundance, ratio (with another entity), or distribution of, e.g., impurities, e.g., host cell proteins, residue from purification processes, viral impurities, and enclosure components.

In some instances, an abatacept signature includes reference criteria or rules for 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 parameters shown in Table 1. In some instances, an abatacept signature comprises reference criteria or rules for two or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53 or 54) of abatacept parameter(s) 1 to 54. In some instances, an abatacept signature comprises predetermined reference criteria or rule(s) for 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 parameters shown in Table 1. In some instances, an abatacept signature comprises reference criteria or rules for one or more, including any combination, or all, of parameter numbers 1 to 54.

In some instances, methods (i.e., evaluation, identification, and production methods) can further include, e.g., one or more of: providing or obtaining a biologic preparation (e.g., such as a glycoprotein drug substance or a precursor thereof); memorializing confirmation or identification of the biologic preparation as abatacept using a recordable medium (e.g., on paper or in a computer readable medium, e.g., in a Certificate of Testing, Certificate of Analysis, Material Safety Data Sheet (MSDS), batch record, or Certificate of Analysis (CofA)); informing a party or entity (e.g., a contractual or manufacturing partner, a care giver or other end-user, a regulatory entity, e.g., the FDA or other U.S., European, Japanese, Chinese or other governmental agency, or another entity, e.g., a compendial entity (e.g., U.S. Pharmacopoeia (USP)) or insurance company) that a biologic preparation is abatacept; selecting the biologic preparation for further processing (e.g., processing (e.g., formulating) the biologic preparation as a drug product (e.g., a pharmaceutical product) if the biologic preparation is identified as abatacept; reprocessing or disposing of the biologic preparation if the biologic preparation is not identified as abatacept.

In some instances, methods (i.e., evaluation, identification, and production methods) include taking action (e.g., physical action) in response to the methods disclosed herein. For example, the biologic preparation is classified, selected, accepted or discarded, released or withheld, processed into a drug product, shipped, moved to a different location, formulated, labeled, packaged, released into commerce, or sold or offered for sale, depending on whether the preselected relationship is met.

In some instances, processing may include formulating, packaging (e.g., in a syringe or vial), labeling, or shipping at least a portion of the glycoprotein preparation. In some instances, processing includes formulating, packaging (e.g., in a syringe or vial), and labeling at least a portion of the biologic as abatacept drug product. Processing can include directing and/or contracting another party to process as described herein.

Definitions

As used herein, a biologic refers to amino acid sequences that include one or more oligosaccharide chains (e.g., glycans) covalently attached thereto. Exemplary amino acid sequences include peptides, polypeptides and proteins. Exemplary biologics include glycosylated antibodies and antibody-like molecules (e.g., Fc fusion proteins). Exemplary antibodies include monoclonal antibodies and/or fragments thereof, polyclonal antibodies and/or fragments thereof, and Fc domain containing fusion proteins (e.g., fusion proteins containing the Fc region of IgG1, or a glycosylated portion thereof). A biologic preparation is a composition or mixture that includes at least one biologic.

As used herein, a CTLA4-Fc fusion protein refers to a genetically engineered fusion protein composed of a modified Fc region of the immunoglobulin IgG1 fused to the extracellular domain of cytotoxic T-lymphocyte-associated antigen 4 (CTLA4) that has at least 95%, 96%, 97%, 98%, 99%, or 100% identity to SEQ ID NO:1.

A biologic preparation (e.g., such as a biologic drug substance or a precursor thereof) included herein is or includes a biologic (e.g., a recombinant fusion protein) that has an amino acid sequence with at least 85% identity to SEQ ID NO:1. In certain embodiments of the biologic, amino acid 29 is alanine and amino acid 104 is leucine. In other embodiments of the biologic, amino acid 29 is not alanine and amino acid 104 is not leucine. In other embodiments of the biologic, amino acid 29 is tyrosine and amino acid 104 is glutamic acid. In other embodiments of the biologic, amino acid 29 is not tyrosine and amino acid 104 is not glutamic acid. In some instances, the amino acid sequence has at least 90%, 91%, 92%, 93%, 94%, 95%, 96%, 97%, 98%, 99%, or 100% identity to SEQ ID NO:1.

In some instances, a biologic preparation (e.g., such as a biologic drug substance or a precursor thereof) can be a sample from a proposed or test batch of a drug substance or drug product. As used herein, a batch of a biologic preparation refers to a single production run of the biologic. Evaluation of different batches thus means evaluation of different production runs or batches. As used herein sample(s) refer to separately procured samples. For example, evaluation of separate samples could mean evaluation of different commercially available containers or vials of the same batch or from different batches. A batch can include a drug product or drug substance.

As used herein, abatacept is the generic, compendial, nonproprietary, or official FDA name for the product marketed in the United States as ORENCIA®.

As used herein, evaluating, e.g., in the evaluation/evaluating, identifying, and/or producing aspects disclosed herein means reviewing, considering, determining, assessing, analyzing, measuring, and/or detecting the presence, absence, level, and/or ratio of one or more abatacept-specific parameters in a biologic preparation to provide information pertaining to the one or more abatacept-specific parameters. In some instances, evaluating can include performing a process that involves a physical change in a sample or another substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Evaluating can include performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent. In some instances, evaluating a biologic preparation includes detecting the presence, absence, level, or ratio of one or more (e.g., two or more when working with ratios) disclosed in Table 1 using methods disclosed in Table 7.

Information (e.g., value(s)) pertaining to an abatacept-specific parameter or an abatacept parameter means information, regardless of form, that describes the presence, absence, abundance, absolute or relative amount, ratio (with another entity), or distribution of a moiety associated with the biologic preparation and/or abatacept. Information is evaluated in a biologic preparation as disclosed herein. Information is also conveyed in an abatacept signature. Information can be qualitative, e.g., present, absent, intermediate, or quantitative, e.g., a numerical value such as a single number, or a range, for a parameter. In some instances, information is from a single sample or batch or a plurality of samples or batches. In some instances, information can be a range or average (or other measure of central tendency), e.g., based on the values from any X samples or batches, e.g., wherein at least X of the samples or batches is being evaluated for commercial release, wherein X is equal to, at least, or no more than, 2, 3, 4, 5, 6, 7, 8, 9, 10, 11, 12, 13, 14, 15, 16, 17, 18, 19, 20, 21, 22, 23, or 24. In some instances, information can be, for example: a statistical function, e.g., an average, of a number of values; a function of another value, e.g., of the presence, distribution or amount of a second entity present in the sample, e.g., an internal standard; a statistical function, e.g., an average, of a number of values; a function of another value, e.g., of the presence, distribution or amount of a second entity present in the sample, e.g., an internal standard; a value, e.g., a qualitative value, e.g., present, absent, "below limit of detection," "within normal limits," or intermediate. In some instances, information can be a quantitative value, e.g., a numerical value such as a single number, a range of values, a "no less than x amount" value, a "no more than x amount" value. In some instances, information can be abundance. Abundance can be expressed in relative terms, e.g., abundance can be expressed in terms of the abundance of a structure in relation to another component in the preparation. E.g., abundance can be expressed as: the abundance of a structure (or a first group of structures) in Table 1 relative to the amount of protein; the abundance of a structure (or a first group of structures) in Table 1 relative to the abundance of a second structure (or second group of structures) in Table 1. Abundance, e.g., abundance of a first structure relative to another structure, can be with regard to the preparation as a whole, a single molecule, or a selected site on the protein backbone. E.g., the parameter can be the relative proportion of a first structure from Table 1 and a second structure from Table 1 at a selected site and the value can be expressed as, e.g., a proportion, ratio or percentage. Information can be expressed in any useful term or unit, e.g., in terms of weight/weight, number/number, number/weight, and weight/number. In many cases, the reference criterion is defined by a range of values.

As used herein, acquire or acquiring (e.g., acquiring information) means obtaining possession of a physical entity, or a value, e.g., a numerical value, by "directly acquiring" or "indirectly acquiring" the physical entity or value. Directly acquiring means performing a process (e.g., performing an assay or test on a sample or "analyzing a sample" as that term is defined herein) to obtain the physical entity or value. Indirectly acquiring refers to receiving the physical entity or value from another party or source (e.g., a third party laboratory that directly acquired the physical entity or value). Directly acquiring a physical entity includes performing a process, e.g., analyzing a sample, that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent. Exemplary analytical methods are shown in Table 7.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way.

These and other aspects of the invention, are described in more detail below and in the claims.

DESCRIPTION OF THE DRAWING

FIG. 1|Amino acid sequence of abatacept (SEQ ID NO: 1).

DETAILED DESCRIPTION

Detailed, high resolution, structural information about ORENCIA® (e.g., related to the presence of signature glycan species or quantitative analyses ascribing site-specificity for backbone modifications) is useful to be able to make and test products that qualify as abatacept, e.g., that are interchangeable versions of ORENCIA®. Such information is also useful in monitoring product changes and controlling structural drift that may occur as a result of manufacturing changes. The art supports, however, that information necessary to be able to make and test products that qualify as abatacept, e.g., that are interchangeable versions of ORENCIA®, or any other branded biologic, is unavailable (see, e.g., Nowicki, "Basic Facts about Biosimilars," Kidney Blood Press. Res., 30:267-272 (2007); Hincal "An Introduction To Safety Issues In Biosimilars/Follow-On Biopharmaceuticals", J. Med. CBR Def., 7:1-18, (2009); Roger, "Biosimilars: current status and future directions," Expert Opin. Biol. Ther., 10(7):1011-1018 (2010); Schellekens et al., Nat. Biotechnol. 28:28-31 (2010); Sekhon et al., Biosimilars, 1:1-11 (2011)). One exemplary report states that "[t]he size and complexity of . . . therapeutic proteins make the production of an exact replica almost impossible; therefore, there are no true generic forms of these proteins . . . Verification of the similarity of biosimilars to innovator medicines remains a key challenge" (Hincal, supra). This disclosure provides, in part, methods and compositions sufficient to make and test products that qualify as abatacept, e.g., that are interchangeable versions of ORENCIA®.

Biologic preparations useful herein can be obtained from any source. In some instances, providing or obtaining a biologic preparation (e.g., such as a biologic drug substance or a precursor thereof), e.g., that is or includes a biologic, can include providing a host cell, e.g., a mammalian host cell (e.g., a CHO cell) that is genetically engineered to express a biologic having an amino acid sequence at least 85% identical to SEQ ID NO:1 (e.g., a genetically engineered cell), wherein amino acid 29 is alanine and amino acid 104 is leucine; culturing the host cell under conditions suitable to express the biologic (e.g., mRNA and/or protein); and, optionally, purifying the expressed biologic, e.g., in the form of a recombinant fusion protein) from the cultured cell, thereby producing a biologic preparation. In some instances, the host cell is genetically engineered to express a biologic having an amino acid sequence at least 90%, 91%, 92%, 93%, 94%, 95%, 96%, 97%, 98%, 99%, or 100% identical to SEQ ID NO:1, wherein the expressed protein forms a recombinant fusion protein composition.

As used herein percent (%) sequence identity with respect to a sequence is defined as the percentage of amino acid residues or nucleotides in a candidate sequence that are identical with the amino acid residues or nucleotides in the reference sequence, after aligning the sequences and introducing gaps, if necessary, to achieve the maximum percent sequence identity. (E.g., gaps can be introduced in one or both of a first and a second amino acid or nucleic acid sequence for optimal alignment and non-homologous sequences can be disregarded for comparison purposes). Alignment for purposes of determining percent sequence identity can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. In one embodiment, the length of a reference sequence aligned for comparison purposes is at least 30%, e.g., at least 40%, e.g., at least 50%, 60%, 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. In some instances a product will include amino acid variants, e.g., species that differ at terminal residues, e.g., at one, two, three, or four N-terminal residues and/or one C-terminal residue (see Table 1). In instances of such cases the sequence identity which is compared is the identity between the primary amino acid sequences of the most abundant active species in each of the products being compared. In some instances sequence identity refers to the amino acid sequence encoded by a nucleic acid that can be used to make the product.

In some instances, an abatacept signature disclosed herein can include 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 of the abatacept parameters (e.g., the reference criterion therefore) shown in Table 1 (e.g., including any combination of two or more (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54) of parameter numbers 1 to 54 shown in Table 1).

In some instances, an abatacept signature disclosed herein can include structures or characteristics (whether intrinsic or extrinsic) of abatacept, e.g., that distinguish abatacept from non-abatacept glycoprotein. Examples of structures or characteristics include: the amount of GalNAc in the preparation (e.g., relative to total glycans of the preparation); the amount of truncated core glycans; the amount of aglycosylated glycans; the amount of each species of high mannose glycans; the amount of sialylated glycans or particular species of sialylated glycans; the ratio of monosialylated:disialylated glycans, the amount of diacetylated sialic acids (NeuXAc2), and the amount of one or more of: NeuGc; NeuAc; Neu5,7,Ac2; Neu5Gc,9Ac; Neu5,8Ac2; Neu5,9Ac2; Neu4,5Ac2. Examples of parameters related to the glycan linkage composition of a biologic preparation can be: the presence or amount of one or more of terminal fucose; terminal mannose; terminal galactose; 2 linked mannose; 3,6 linked mannose; terminal GlcNAc; terminal GalNAc; 4 linked GlcNAc; 4,6 linked GlcNAc. A parameter may also be the ratio of one of these to another or to another property. Examples of parameters related to the glycoform composition of a biologic preparation include: the absence or presence of one or more specific glycoforms (e.g., one or more glycoforms described in Table 1); the amount or abundance of a specific glycoform in the preparation relative to total glycoforms (e.g., in a w/w basis); the ratio of one particular glycoform to another. Examples of parameters related to post-translational modification in the preparation include: the absence or presence of one or more specific post-translational modification; the abundance or distribution of one or more specific post-translational modification.

In some instances, the present disclosure includes determining whether information evaluated for a biologic preparation meets an abatacept signature, e.g., by comparing the information with the abatacept signature and/or confirming that the information has a defined (e.g., predefined) relationship with the abatacept signature.

In some instances, methods disclosed herein can be used to confirm the identity and/or quality of abatacept preparations. For example, methods can include assessing preparations (e.g., samples, lots, and/or batches) of a test biologic to confirm whether the test biologic qualifies as abatacept, and, optionally, qualifying the test biologic as abatacept if qualifying criteria (e.g. predefined qualifying criteria) are met; thereby evaluating, identifying, and/or producing (e.g., manufacturing) abatacept.

Methods of the disclosure have a variety of applications and include, e.g., quality control at different stages of manufacture, analysis of abatacept preparations prior to or after completion of manufacture (e.g., prior to or after distribution to a fill/finish environment or facility), prior to or after release into commerce (e.g., before distribution to a pharmacy, a caregiver, a patient, or other end-user). Thus, the preparation can be any preparation that potentially comprises abatacept. In an embodiment the abatacept preparation is a drug substance (an active pharmaceutical ingredient or "API") or a drug product (an API formulated for use in a subject such as a human patient). In an embodiment the preparation is from a stage of manufacture or use that is prior to release to care givers or other end-users; prior to packaging into individual dosage forms, such as syringes, pens, vials, or multi-dose vials; prior to determination that the batch can be commercially released, prior to production of a Certificate of Testing, Material Safety Data Sheet (MSDS) or Certificate of Analysis (CofA) of the preparation. In an embodiment, the biologic preparation is from an intermediate step in production, e.g., it is after secretion of the biologic from a cell but prior to purification of drug substance.

Evaluations from methods of the invention are useful for guiding, controlling, or implementing a number of activities or steps in the process of making, distributing, and monitoring and providing for the safe and efficacious use of abatacept. Thus, in an embodiment, e.g., responsive to the evaluation, e.g., depending on whether a criterion is met, a decision or step is taken. The method can further include one or both of the decision to take the step and/or carrying out the step itself. E.g., the step can include one in which the preparation (or another preparation for which the preparation is representative) is: classified; selected; accepted or discarded; released or processed into a drug product; rendered unusable for commercial release, e.g., by labeling it, sequestering it, or destroying it; passed on to a subsequent step in manufacture; reprocessed (e.g., the preparation may undergo a repetition of a previous process step or subjected to a corrective process); formulated, e.g., into drug substance or drug product; combined with another component, e.g., an excipient, buffer or diluent; disposed into a container; divided into smaller aliquots, e.g., unit doses, or multi-dose containers; combined with another preparation of abatacept; packaged; shipped; moved to a different location; combined with another element to form a kit; combined, e.g., placed into a package with a delivery device, diluent, or package insert; released into commerce; sold or offered for sale; delivered to a care giver or other end-user; or administered to a subject. E.g., based on the result of the determination or whether one or more subject entities is present, or upon comparison to a reference standard, the batch from which the preparation is taken can be processed, e.g., as just described.

Methods described herein may include making a decision: (a) as to whether a preparation may be formulated into drug substance or drug product; (b) as to whether a preparation may be reprocessed (e.g., the preparation may undergo a repetition of a previous process step); or (c) that the preparation is not suitable for formulation into drug substance or drug product. In instances the method comprises: formulating as referred to in step (a), reprocessing as referred to in step (b), or rendering the preparation unusable for commercial release, e.g., by labeling it or destroying it, as referred to in step (c).

Parameter Evaluation

The amino acid sequence of abatacept (ORENCIA®) is disclosed herein as SEQ ID NO:1.

Parameters disclosed herein can be analyzed by any available suitable method. In some instances, glycan structure and composition as described herein are analyzed, for example, by one or more, enzymatic, chromatographic, mass spectrometry (MS), chromatographic followed by MS, electrophoretic methods, electrophoretic methods followed by MS, nuclear magnetic resonance (NMR) methods, and combinations thereof. Exemplary enzymatic methods include contacting a glycoprotein preparation with one or more enzymes under conditions and for a time sufficient to release one or more glycans (e.g., one or more exposed glycans). In some instances, the one or more enzymes include PNGase F. Exemplary chromatographic methods include, but are not limited to, Strong Anion Exchange chromatography using Pulsed Amperometric Detection (SAX-PAD), liquid chromatography (LC), high performance liquid chromatography (HPLC), ultra performance liquid chromatography (UPLC), thin layer chromatography (TLC), amide column chromatography, and combinations thereof. Exemplary mass spectrometry (MS) include, but are not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof. Exemplary electrophoretic methods include, but are not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof. Exemplary nuclear magnetic resonance (NMR) include, but are not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In some instances, techniques described herein may be combined with one or more other technologies for the detection, analysis, and or isolation of glycans or glycoproteins. For example, in certain instances, glycans are analyzed in accordance with the present disclosure using one or more available methods (to give but a few examples, see Anumula, Anal. Biochem. 350(1):1, 2006; Klein et al., Anal. Biochem., 179:162, 1989; and/or Townsend, R. R. Carbohydrate Analysis" High Performance Liquid Chromatography and Capillary Electrophoresis., Ed. Z. El Rassi, pp 181-209, 1995, each of which is incorporated herein by reference in its entirety). For example, in some instances, glycans are characterized using one or more of chromatographic methods, electrophoretic methods, nuclear magnetic resonance methods, and combinations thereof.

In some instances, methods for evaluating one or more abatacept-specific parameters, e.g., in a biologic preparation, e.g., one or more of abatacept parameters disclosed in Table 1 in a biologic preparation are known in the art and/or are disclosed in Table 7:

TABLE 7

| Method(s) | Relevant literature | Parameter |
|---|---|---|
| Peptide LC-MS | Ivancic et al., Anal. Biochem., 400: 25-32 (2010) Bongers et al., J. Chrom A, 1218: 8140-49 (2011) | Glycan(s) (e.g., N-linked glycan, exposed N-linked glycan, O-linked glycan, exposed O-linked glycan, glycan detection, glycan identification, and characterization; site specific glycation; glycoform detection; percent glycosylation; and/or aglycosyl) |
| Peptide LC-MS (reducing/non-reducing) | Dick et al., Biotechnol. Bioeng., 100:1132-1143 (2008) | C-terminal lysine |
| LC-MS (reducing/non-reducing/alkylated) | Dick et al., Biotechnol. Bioeng., 100:1132-1143 (2008) | |
| Weak cation exchange (WCX) chromatography | Dick et al., Biotechnol. Bioeng., 100:1132-1143 (2008) | |
| Anion cation exchange (AEX) chromatography +/− sialidase treatment | Royle et al., Methods Mol. Biol., 347: 125-43 (2006) Takahashi, J. Chrom. A, 720: 217-25 (1996) | Charged distribution of glycans, sulfate content |
| DMB-sialic acid HPLC | Hara et al. Chromatography., B: Biomed. 377: 111-119 (1986) Varki et al. Anal. Biochem. 137, 236-247 (1984) | Sialic acid content |

References listed in Table 7 are hereby incorporated by reference in their entirety or, in the alternative, to the extent that they pertain to one or more of the methods disclosed in Table 7. Other methods for evaluating one or more abatacept specific parameters are disclosed in the examples.

EXAMPLES

Example 1: Characterization of Abatacept

An ORENCIA® sample was analyzed to determine the amino acid sequence of the fusion protein. The sequence of the protein is shown as SEQ ID NO:1 (FIG. 1).

Characterization of abatacept was performed by orthogonal methods. Samples of abatacept were analyzed and measurements were made including use of glycan profiling, glycoform analysis, post-translational modification analysis, and analysis of other intrinsic and extrinsic structures or features. In one method, described herein, abatacept samples were processed by digesting with trypsin in mass spectrometry compatible digestion buffer compatible, performed using pressure cycling technology. Digestion was performed using a BAROCYCLER® NEP 2320 (Pressure Biosciences) with the Barocycler settings: Temperature: 37° C.; high pressure: 20,000 PSI; time 1 (high pressure): 90 sec; Time 2 (ambient pressure) 20 sec, with 40 cycles, and total digestion time of about 75 minutes. Digests were then analyzed by C18 reversed phase HPLC-MS peptide mapping run utilizing an Orbitrap XL, with multiple sections for the LC gradient to separate each cluster of glycopeptides within each glycosylation site and multiple tune methods to coordinate with the multiple sections of the LC gradient. Of the abatacept structures or features that were measured or determined, 54 were determined to be abatacept parameters, i.e., parameters of abatacept that distinguish abatacept from non-abatacept drug products. These 54 abatacept parameters and values are listed in Table 1.

Example 2: Qualification of Biologic Preparations for Commercial Release as Abatacept As disclosed herein, one or more, including a subset, class, multiple classes or all, of the reference criteria shown in Table 1, may be included in a specification for commercial release of abatacept under Section 351(k) of the PHS Act. This concept is exemplified in Table 8, in which parameters A-J are reference criteria defining the abatacept fingerprint, wherein each of parameters A-J is one of parameters 1 to 54 in Table 1. Table 8 also illustrates comparison of these reference criteria with input values corresponding thereto for two hypothetical test biologic preparations (Test Biologic Preparations A and B) having amino acid sequence with identity to SEQ ID NO:1.

TABLE 8

| Parameter | Comparison of input values for Test Biologic Preparation A with reference criterion | Comparison of input values for Test Biologic Preparation B with reference criterion |
|---|---|---|
| A | ✓ | ✓ |
| B | ✓ | ✓ |
| C | ✓ | ✓ |
| D | ✓ | ✓ |
| E | ✓ | ✓ |
| F | ✓ | ✓ |
| G | ✓ | ✓ |
| H | ✓ | ✓ |
| I |  | ✓ |
| J |  | ✓ |

✓Illustrates that a value meets the reference criterion/rule. Blank illustrates that a value does not meet the reference criterion/rule.

According to Table 8, Test Biologic Preparation A would not qualify as abatacept and thus would not be processed as abatacept because input values for each of one or more parameters for the test biologic preparation do not meet the corresponding reference criterion for that parameter. In contrast, Test Biologic Preparation B would qualify as abatacept, as it meets the abatacept fingerprint, and thus would be processed as abatacept because input values for each of one or more parameters for the test biologic preparation meet the corresponding reference criterion for that parameter.

Example 3: Qualification of Biologic Preparations for Commercial Release

As disclosed herein, one or more, including a subset, class, multiple classes or all, of the reference criteria shown in Table 1, may be included in a specification for commercial release of a pharmaceutical product comprising a CTLA4-Fc fusion. This concept is exemplified in Table 9, in which parameters A-J represent reference criteria for a subset or class of parameters 1 to 54 in Table 1. Table 9 also illustrates comparison of the reference criteria (the signature or fingerprint representing the specification for commercial release of a pharmaceutical product comprising a CTLA4-Fc fusion) with input values corresponding thereto for two hypothetical test CTLA4-Fc fusion preparations (Test Biologic Preparations A and B) having amino acid sequence with identity to SEQ ID NO:1. In this example, only a subset of input values corresponding to A-J meets the criterion.

TABLE 9

| Parameter | Comparison of input values for Test Biologic Preparation A with reference criterion | Comparison of input values for Test Biologic Preparation B with reference criterion |
|---|---|---|
| A | ✓ |  |
| B | ✓ |  |
| C | ✓ | ✓ |
| D | ✓ | ✓ |
| E | ✓ | ✓ |
| F | ✓ | ✓ |
| G | ✓ | ✓ |
| H | ✓ | ✓ |
| I |  | ✓ |
| J |  | ✓ |

✓Illustrates that a value meets the reference criterion/rule. Blank illustrates that a value does not meet the reference criterion/rule.

According to Table 9, Test Biologic Preparation A and B would qualify as CTLA4-Fc fusion pharmaceutical product and thus could be processed into a CTLA4-Fc fusion pharmaceutical product because input values for a subset of reference criterion A-J meet the reference criteria therefor. Test Biologic Preparation A and B shown here would not, however, qualify as abatacept as they do not meet the abatacept fingerprint.

While the methods have been described in conjunction with various instances and examples, it is not intended that the methods be limited to such instances or examples. On the contrary, the methods encompass various alternatives, modifications, and equivalents, as will be appreciated by those of skill in the art.

What is claimed is:

1. A method of manufacturing an abatacept drug product, comprising:
   providing or obtaining a test glycoprotein preparation;
   acquiring a value for each of a plurality of parameters listed in Table 1 for the test glycoprotein preparation, wherein the values for the plurality of parameters in combination distinguish abatacept from a non-abatacept glycoprotein; and wherein the plurality of abatacept parameters comprise the percent aglycosylation at O129 and the percent aglycosylation at O139; and
   processing, or directing the processing of, at least a portion of the test glycoprotein preparation as abatacept drug product if the values for the plurality for the test glycoprotein preparation meet the corresponding reference criteria shown in Table 1 for said parameters, wherein the reference criteria include 36.2-59.3% aglycosylation at O129 and 0.8-2.7% aglycosylation at O139, or
   taking an alternative action if the values for the plurality of abatacept parameters for the test glycoprotein preparation do not meet the corresponding reference criteria shown in Table 1 for the parameters, including 36.2-59.3% aglycosylation at O129 and 0.8-2.7% aglycosylation at O139;
   thereby manufacturing an abatacept drug product,
   wherein the test glycoprotein preparation comprises a glycoprotein composition having an amino acid sequence with at least 98% identity to SEQ ID NO:1, and wherein amino acid 29 is alanine and amino acid 104 is leucine.

2. The method of claim 1, wherein the plurality of abatacept parameters comprises a total of:
   2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54 of the abatacept parameters listed in Table 1.

3. The method of claim 1, wherein the test glycoprotein preparation has an amino acid sequence with 100% identity to SEQ ID NO: 1.

4. The method of claim 1, wherein the value is directly obtained by performing an analytical test on the test glycoprotein preparation.

5. The method of claim 4, wherein the value is directly obtained using a method provided in Table 7.

6. The method of claim 1, wherein the processing step comprises combining the test glycoprotein preparation with an excipient or buffer.

7. The method of claim 1, wherein the processing step comprises one or more of: formulating the test glycoprotein preparation; processing the test glycoprotein preparation into a drug product; combining the test glycoprotein preparation with a second component; changing the concentration of the glycoprotein in the preparation; lyophilizing the test glycoprotein preparation; combining a first and second aliquot of the glycoprotein to provide a third, larger, aliquot; dividing the test glycoprotein preparation into smaller aliquots; disposing the test glycoprotein preparation into a container; packaging the test glycoprotein preparation; associating a container comprising the test glycoprotein preparation with a label; and shipping or moving the test glycoprotein to a different location.

8. The method of claim 1, wherein the processed glycoprotein is approved under Section 351(k) of the Public Health Service (PHS) Act.

9. The method of claim 1, wherein the processed glycoprotein is not approved under a BLA under Section 351(a) of the PHS Act.

10. The method of claim 1, wherein the input value is acquired for one, two or more samples or batches.

11. The method of claim 1, wherein the input value(s) for the test glycoprotein preparation comprise an average of a range of values for the parameter for multiple batches or samples of the test glycoprotein.

12. The method of claim 1, wherein the plurality of the reference criteria shown in Table 1 are a specification for commercial release of an abatacept drug product under Section 351(k) of the Public Health Service Act.

13. The method of claim 1, comprising:
   providing a host cell that is genetically engineered to express a CTLA4-Fc fusion protein having an amino acid sequence with at least about 98% identity to SEQ ID NO:1, wherein amino acid 29 is alanine and amino acid 104 is leucine;
   culturing the host cell under conditions whereby the cell expresses the CTLA4-Fc fusion protein; and
   harvesting the CTLA4-Fc fusion protein from the host cell culture to produce a test glycoprotein preparation.

14. The method of claim 13, wherein:
   the host cell is genetically engineered to express glycoprotein having the amino acid sequence of SEQ ID NO: 1.

15. The method of claim 1, wherein the plurality of abatacept parameters comprises at least one abatacept parameter listed in Table 1 in addition to parameters 41 and 43.

16. The method of claim 1, wherein the processed drug product is structurally similar to abatacept so as to qualify as an abatacept drug product.

17. The method claim 1, wherein the plurality of the reference criterion shown in Table 1 is a product acceptance criterion.

18. The method of claim 1, wherein taking an alternative action comprises (a) reprocessing, (b) disposing of, or (c) rendering the test glycoprotein preparation unusable for commercial release by labeling or destroying it.

19. The method of claim 1, wherein the plurality of abatacept parameters further comprises at least one of parameters 35, 36, 37, 39, 40, and 42.

20. The method of claim 1, wherein the plurality of abatacept parameters further comprises at least two of parameters 35, 36, 37, 39, 40, and 42.

* * * * *

SEQUENCE LISTING

<160> NUMBER OF SEQ IDS NOS: 1

<210> SEQ ID NO 1
<211> LENGTH: 357
<212> TYPE: PRT
<213> ORGANISM: Artificial Sequence
<220> FEATURE:
<223> OTHER INFORMATION: Synthetic Construct

<400> SEQUENCE: 1

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335
```

```
Val Met His Glu Ala Leu His Asn His Tyr Thr Gln Lys Ser Leu Ser
            340                 345                 350

Leu Ser Pro Gly Lys
        355
```